US006551576B1

(12) United States Patent
Unger et al.

(10) Patent No.: US 6,551,576 B1
(45) Date of Patent: *Apr. 22, 2003

(54) CONTAINER WITH MULTI-PHASE COMPOSITION FOR USE IN DIAGNOSTIC AND THERAPEUTIC APPLICATIONS

(75) Inventors: Evan C. Unger, Tucson, AZ (US); Terry Matsunaga, Tucson, AZ (US); David Yellowhair, Tucson, AZ (US)

(73) Assignee: Bristol-Myers Squibb Medical Imaging, Inc., Princeton, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/052,075

(22) Filed: Mar. 31, 1998

Related U.S. Application Data

(60) Division of application No. 08/741,598, filed on Nov. 1, 1996, which is a division of application No. 08/307,305, filed on Sep. 16, 1994, which is a continuation-in-part of application No. 08/159,687, filed on Nov. 30, 1993, now Pat. No. 5,585,112, which is a continuation-in-part of application No. 08/076,239, filed on Jun. 11, 1993, now Pat. No. 5,469,854, which is a continuation-in-part of application No. 07/717,084, filed on Jun. 18, 1991, now Pat. No. 5,228,446, and a continuation-in-part of application No. 07/716,899, filed on Jun. 18, 1991, now abandoned, which is a continuation-in-part of application No. 07/569,828, filed on Aug. 20, 1990, now Pat. No. 5,088,499, which is a continuation-in-part of application No. 07/455,707, filed on Dec. 22, 1989, now abandoned, said application No. 08/307,305, is a continuation-in-part of application No. 08/160,232, filed on Nov. 30, 1993, now Pat. No. 5,542,935, which is a continuation-in-part of application No. 08/076,250, filed on Jun. 11, 1993, now Pat. No. 5,580,575, which is a continuation-in-part of application No. 07/717,084, filed on Jun. 18, 1991, now Pat. No. 5,228,446, and a continuation-in-part of application No. 07/716,899, filed on Jun. 18, 1991, now abandoned, which is a continuation-in-part of application No. 07/569,828, which is a continuation-in-part of application No. 07/455,707, filed on Dec. 22, 1989, now abandoned, said application No. 08/307,305, is a continuation-in-part of application No. 08/212,553, filed on Mar. 11, 1994, now abandoned, which is a continuation-in-part of application No. 08/076,239, filed on Jun. 11, 1993, and a continuation-in-part of application No. 08/076,250, filed on Jun. 11, 1993.

(51) Int. Cl.[7] .............................. A61B 8/00; A61K 9/127
(52) U.S. Cl. ...................... 424/9.52; 424/450; 424/9.51; 424/9.321; 424/9.3; 424/9.34; 424/9.5
(58) Field of Search ................... 424/9.52, 9.5, 424/9.51, 450, 9.321, 9.3, 9.34

(56) References Cited

U.S. PATENT DOCUMENTS 3,015,128 A 1/1962 Sommerville et al. ........ 18/2.6
3,291,843 A 12/1966 Fritz et al. .................. 260/614

(List continued on next page.)

FOREIGN PATENT DOCUMENTS

| AU | 641363 | 3/1990 |
|---|---|---|
| AU | B-30351/89 | 3/1993 |
| DE | 25 21 003 | 8/1976 |
| EP | 0 052 575 | 5/1982 |
| EP | 0 107 559 | 5/1984 |
| EP | 0 077 752 B1 | 3/1986 |
| EP | 0 243 947 | 4/1987 |
| EP | 0 231 091 | 8/1987 |
| EP | 0 272 091 | 6/1988 |
| EP | 0 320 433 A2 | 12/1988 |
| EP | 0 324 938 | 7/1989 |
| EP | 0 338 971 | 10/1989 |
| EP | 357163 A1 | 3/1990 |
| EP | 0 361 894 | 4/1990 |
| EP | 0 216 730 | 1/1991 |
| EP | 0 467 031 A2 | 5/1991 |
| EP | 441468 A2 | 8/1991 |
| EP | 0 357 164 B1 | 10/1991 |
| EP | 0 458 745 A1 | 11/1991 |
| EP | 0 314 764 B1 | 9/1992 |
| EP | 0 554 213 A1 | 8/1993 |
| EP | 0 586 875 | 3/1994 |
| EP | 0 614 656 A1 | 9/1994 |
| EP | 0 727 225 A2 | 8/1996 |
| FR | 2 700 952 | 8/1994 |
| GB | 1044680 | 10/1966 |
| GB | 2193095 A | 2/1988 |
| JP | 62 286534 | 12/1987 |
| JP | SHO 63-60943 | 3/1988 |
| WO | WO 80/02365 | 11/1980 |
| WO | WO 82/01642 | 5/1982 |
| WO | WO 85/01161 | 3/1985 |
| WO | WO 86/00238 | 1/1986 |
| WO | WO 86/01103 | 2/1986 |
| WO | WO 89/05040 | 6/1989 |
| WO | WO 90/01952 | 3/1990 |
| WO | WO 90/04384 | 5/1990 |
| WO | WO 90/04943 | 5/1990 |
| WO | WO 91/00086 | 1/1991 |
| WO | WO 91/03267 | 3/1991 |

(List continued on next page.)

OTHER PUBLICATIONS

Nomura et al., "US Contrast Enhancement of Hepatic Tumor with Helium Gas Microbubbles: A Preliminary Report", *Jpn. J. Med. Ultrasonics*, 1991, 18(5), (Japanese with English language abstract).

(List continued on next page.)

Primary Examiner—Russell Travers
Assistant Examiner—Shahnam J Sharareh
(74) *Attorney, Agent, or Firm*—Woodcock Washburn LLP

(57) ABSTRACT

A container comprising an aqueous lipid suspension and a gaseous phase substantially separate from the aqueous stabilizing phase, useful in diagnostic imaging such as ultrasound and magnetic resonance imaging and in therapeutic applications, is disclosed.

155 Claims, 3 Drawing Sheets

U.S. PATENT DOCUMENTS

| | | | |
|---|---|---|---|
| 3,293,114 A | 12/1966 | Kenaga et al. | 162/168 |
| 3,479,811 A | 11/1969 | Walters | 57/153 |
| 3,488,714 A | 1/1970 | Walters et al. | 161/161 |
| 3,532,500 A | 10/1970 | Priest et al. | 96/91 |
| 3,557,294 A | 1/1971 | Dear et al. | 424/342 |
| 3,594,326 A | 7/1971 | Himmel et al. | 252/316 |
| 3,615,972 A | 10/1971 | Morehouse et al. | 156/79 |
| 3,650,831 A | 3/1972 | Jungermann et al. | 134/27 |
| 3,732,172 A | 5/1973 | Herbig et al. | 252/316 |
| 3,873,564 A | 3/1975 | Schneider et al. | 270/309.6 |
| 3,945,956 A | 3/1976 | Garner | 270/2.5 B |
| 3,960,583 A | 6/1976 | Netting et al. | 106/122 |
| 3,968,203 A | 7/1976 | Spitzer et al. | 424/47 |
| 4,027,007 A | 5/1977 | Messina | 424/46 |
| 4,089,801 A | 5/1978 | Schneider | 252/316 |
| 4,108,806 A | 8/1978 | Cohrs et al. | 521/54 |
| 4,138,383 A | 2/1979 | Rembaum et al. | 270/29.7 H |
| 4,162,282 A | 7/1979 | Fulwyler et al. | 274/9 |
| 4,179,546 A | 12/1979 | Garner et al. | 521/56 |
| 4,192,859 A | 3/1980 | Mackaness et al. | 424/5 |
| 4,224,179 A | 9/1980 | Schneider | 252/316 |
| 4,229,360 A | 10/1980 | Schneider et al. | 424/9 |
| 4,265,251 A | 5/1981 | Tickner | 128/660 |
| 4,276,885 A | 7/1981 | Tickner et al. | 128/660 |
| 4,310,505 A | 1/1982 | Baldeschwieler et al. | 424/1 |
| 4,310,506 A | 1/1982 | Baldeschwieler et al. | 424/1 |
| 4,315,514 A | 2/1982 | Drewes et al. | 128/653 |
| 4,331,654 A | 5/1982 | Morris | 424/38 |
| 4,342,826 A | 8/1982 | Cole | 435/7 |
| 4,344,929 A | 8/1982 | Bonsen et al. | 424/15 |
| 4,420,442 A | 12/1983 | Sands | 274/13 |
| 4,421,562 A | 12/1983 | Sands et al. | 106/75 |
| 4,427,330 A | 1/1984 | Sears | 270/403 |
| 4,427,649 A | 1/1984 | Dingle et al. | 424/38 |
| 4,428,924 A | 1/1984 | Millington | 424/4 |
| 4,442,843 A | 4/1984 | Rasor et al. | 128/660 |
| 4,466,442 A | 8/1984 | Hilmann et al. | 128/653 |
| 4,530,360 A | 7/1985 | Duarte | 128/419 F |
| 4,533,254 A | 8/1985 | Cook et al. | 366/176 |
| 4,534,899 A | 8/1985 | Sears | 270/403 |
| 4,540,629 A | 9/1985 | Sands et al. | 428/402 |
| 4,544,545 A | 10/1985 | Ryan et al. | 424/1.1 |
| 4,549,892 A | 10/1985 | Baker et al. | 65/21.4 |
| 4,569,836 A | 2/1986 | Gordon | 424/1 |
| 4,572,203 A | 2/1986 | Feinstein | 128/661 |
| 4,586,512 A | 5/1986 | Do-huu et al. | 128/660 |
| 4,603,044 A | 7/1986 | Geho et al. | 424/9 |
| 4,615,879 A | 10/1986 | Runge et al. | 424/9 |
| 4,620,546 A | 11/1986 | Aida et al. | 128/660 |
| 4,646,756 A | 3/1987 | Watmough et al. | 128/804 |
| 4,657,756 A | 4/1987 | Rasor et al. | 424/9 |
| 4,658,828 A | 4/1987 | Dory | 128/660 |
| 4,663,161 A | 5/1987 | Mannino et al. | 424/89 |
| 4,675,310 A | 6/1987 | Chapman et al. | 514/6 |
| 4,681,119 A | 7/1987 | Rasor et al. | 128/660 |
| 4,684,479 A | 8/1987 | D'Arrigo | 252/307 |
| 4,689,986 A | 9/1987 | Carson et al. | 73/19 |
| 4,693,999 A | 9/1987 | Axelsson et al. | 514/174 |
| 4,718,433 A | 1/1988 | Feinstein | 128/660 |
| 4,728,575 A | 3/1988 | Gamble et al. | 428/402.2 |
| 4,728,578 A | 3/1988 | Higgins et al. | 428/462 |
| 4,731,239 A | 3/1988 | Gordon | 424/9 |
| 4,737,323 A | 4/1988 | Martin et al. | 274/4.3 |
| 4,774,958 A | 10/1988 | Feinstein | 128/660.01 |
| 4,775,522 A | 10/1988 | Clark, Jr. | 424/9 |
| 4,776,991 A | 10/1988 | Farmer et al. | 274/4.3 |
| 4,781,871 A | 11/1988 | West, III et al. | 274/4.3 |
| 4,789,501 A | 12/1988 | Day et al. | 252/645 |
| 4,790,891 A | 12/1988 | Halliday et al. | 149/2 |
| 4,822,534 A | 4/1989 | Lencki et al. | 274/4.3 |
| 4,830,858 A | 5/1989 | Payne et al. | 424/450 |
| 4,834,964 A | 5/1989 | Rosen | 424/9 |
| 4,844,882 A | 7/1989 | Widder et al. | 424/9 |
| 4,863,717 A | 9/1989 | Keana | 424/9 |
| 4,865,836 A | 9/1989 | Long, Jr. | 424/5 |
| 4,877,561 A | 10/1989 | Iga et al. | 274/4.3 |
| 4,893,624 A | 1/1990 | Lele | 128/399 |
| 4,895,719 A | 1/1990 | Radhakrishnan | 424/45 |
| 4,898,734 A | 2/1990 | Mathiowitz et al. | 424/427 |
| 4,900,540 A | 2/1990 | Ryan et al. | 424/9 |
| 4,918,065 A | 4/1990 | Stindl et al. | 514/179 |
| 4,919,895 A | 4/1990 | Heldebrant et al. | 422/129 |
| 4,921,706 A | 5/1990 | Roberts et al. | 424/450 |
| 4,927,623 A | 5/1990 | Long, Jr. | 424/5 |
| 4,933,121 A | 6/1990 | Law et al. | 264/4.3 |
| 4,938,947 A | 7/1990 | Nicolau et al. | 424/1.1 |
| 4,957,656 A | 9/1990 | Cerny et al. | 252/311 |
| 4,981,692 A | 1/1991 | Popescu et al. | 424/422 |
| 4,984,573 A | 1/1991 | Leunbach | 128/653 |
| 4,985,550 A | 1/1991 | Charpiot et al. | 536/18.4 |
| 4,987,154 A | 1/1991 | Long, Jr. | 514/772 |
| 4,993,415 A | 2/1991 | Long | 128/653 A |
| 4,996,041 A | 2/1991 | Arai et al. | 424/9 |
| 5,000,960 A | 3/1991 | Wallach | 424/450 |
| 5,004,611 A | 4/1991 | Leigh | 424/450 |
| 5,008,050 A | 4/1991 | Cullis et al. | 274/4.3 |
| 5,008,109 A | 4/1991 | Tin | 424/422 |
| 5,013,556 A | 5/1991 | Woodle et al. | 424/450 |
| 5,019,370 A | 5/1991 | Jay et al. | 424/4 |
| 5,045,304 A | 9/1991 | Schneider et al. | 424/9 |
| 5,049,388 A | 9/1991 | Knight et al. | 424/450 |
| 4,229,360 A | 11/1991 | Schneider et al. | 270/403 |
| 5,078,994 A | 1/1992 | Nair et al. | 424/501 |
| 5,088,499 A | 2/1992 | Unger | 128/662.2 |
| 5,107,842 A | 4/1992 | Levene et al. | 128/662.02 |
| 5,114,703 A | 5/1992 | Wolf et al. | 424/5 |
| 5,123,414 A | 6/1992 | Unger | 128/654 |
| 5,135,000 A | 8/1992 | Akselrod et al. | 128/662.02 |
| 5,137,928 A | 8/1992 | Erbel et al. | 521/56 |
| 5,141,738 A | 8/1992 | Rasor et al. | 424/2 |
| 5,147,631 A | 9/1992 | Glajch et al. | 424/9 |
| 5,149,319 A | 9/1992 | Unger | 604/22 |
| 5,171,755 A | 12/1992 | Kaufman | 514/759 |
| 5,186,922 A | 2/1993 | Shell et al. | 128/654 |
| 5,190,766 A | 3/1993 | Ishihara | 424/489 |
| 5,190,982 A | 3/1993 | Erbel et al. | 521/56 |
| 5,192,549 A | 3/1993 | Barenolz et al. | 424/450 |
| 5,194,266 A | 3/1993 | Abra et al. | 424/450 |
| 5,195,520 A | 3/1993 | Schlief et al. | 128/660.02 |
| 5,196,183 A | 3/1993 | Yudelson et al. | 424/9 |
| 5,196,348 A | 3/1993 | Schweighardt et al. | 436/173 |
| 5,198,225 A | 3/1993 | Meybeck et al. | 424/450 |
| 5,205,287 A | 4/1993 | Erbel et al. | 128/632 |
| 5,205,290 A | 4/1993 | Unger | 128/653.4 |
| 5,209,720 A | 5/1993 | Unger | 604/22 |
| 5,213,804 A | 5/1993 | Martin et al. | 424/450 |
| 5,215,680 A | 6/1993 | D'Arrigo | 252/307 |
| 5,219,538 A | 6/1993 | Henderson et al. | 428/402.2 |
| 5,228,446 A | 7/1993 | Unger et al. | 128/662.02 |
| 5,230,882 A | 7/1993 | Unger | 424/9 |
| 5,247,935 A | 9/1993 | Cline et al. | 128/653.2 |
| 5,271,928 A | * 12/1993 | Schneider et al. | 424/9 |
| 5,281,408 A | 1/1994 | Unger | 424/4 |
| 5,305,757 A | 4/1994 | Unger et al. | 128/662.02 |
| 5,310,540 A | 5/1994 | Giddey et al. | 424/9 |
| 5,315,997 A | 5/1994 | Widder et al. | 128/653.3 |
| 5,315,998 A | 5/1994 | Tachibana et al. | 128/660.01 |
| 5,316,771 A | 5/1994 | Barenholz et al. | 424/450 |
| 5,334,381 A | 8/1994 | Unger | 424/9 |
| 5,339,814 A | 8/1994 | Lasker | 128/653.4 |
| 5,344,930 A | 9/1994 | Riess et al. | 544/84 |

| | | | |
|---|---|---|---|
| 5,350,571 A | 9/1994 | Kaufman et al. | 424/9 |
| 5,352,435 A | 10/1994 | Unger | 424/9 |
| 5,354,549 A | 10/1994 | Klaveness et al. | 424/3 |
| 5,358,702 A | 10/1994 | Unger | 424/9 |
| 5,362,477 A | 11/1994 | Moore et al. | 424/9 |
| 5,362,478 A | 11/1994 | Desai et al. | 424/9 |
| 5,380,519 A | 1/1995 | Schneider et al. | 424/9 |
| 5,393,524 A | 2/1995 | Quay | 424/9 |
| 5,409,688 A | 4/1995 | Quay | 424/9 |
| 5,410,516 A | 4/1995 | Uhlendorf et al. | 367/7 |
| 5,413,774 A | 5/1995 | Schneider et al. | 424/9.51 |
| 5,425,366 A | 6/1995 | Reinhardt et al. | 128/662.02 |
| 5,433,204 A | 7/1995 | Olson | 128/661.08 |
| 5,445,813 A | 8/1995 | Schneider et al. | 424/9.51 |
| 5,456,900 A | 10/1995 | Unger | 424/9.4 |
| 5,469,854 A | 11/1995 | Unger et al. | 128/662.02 |
| 5,470,582 A | 11/1995 | Supersaxo et al. | 424/489 |
| 5,485,839 A | 1/1996 | Aida et al. | 128/653.1 |
| 5,487,390 A | 1/1996 | Cohen et al. | 128/662.02 |
| 5,496,535 A | 3/1996 | Kirkland | 424/9.37 |
| 5,498,421 A | 3/1996 | Grinstaff et al. | 424/450 |
| 5,501,863 A | 3/1996 | Rössling et al. | 424/489 |
| 5,502,094 A | 3/1996 | Moore et al. | 524/145 |
| 5,505,932 A | 4/1996 | Grinstaff et al. | 424/9.3 |
| 5,508,021 A | 4/1996 | Grinstaff et al. | 424/9.322 |
| 5,527,521 A | 6/1996 | Unger | 424/93 |
| 5,529,766 A | 6/1996 | Klaveness et al. | 424/9.52 |
| 5,531,980 A | 7/1996 | Schneider et al. | 424/9.52 |
| 5,536,489 A | 7/1996 | Lohrmann et al. | 424/9.52 |
| 5,536,490 A | 7/1996 | Klaveness et al. | 424/9.52 |
| 5,540,909 A | 7/1996 | Schutt | 424/9.52 |
| 5,542,935 A | 8/1996 | Unger et al. | 604/190 |
| 5,545,396 A | 8/1996 | Albert et al. | 424/93 |
| 5,547,656 A | 8/1996 | Unger | 424/9.4 |
| 5,552,133 A | 9/1996 | Lambert et al. | 424/9.52 |
| 5,552,155 A | 9/1996 | Bailey et al. | 424/450 |
| 5,556,372 A | 9/1996 | Talish et al. | 601/2 |
| 5,556,610 A | 9/1996 | Yan et al. | 424/9.52 |
| 5,558,092 A | 9/1996 | Unger et al. | 128/660.03 |
| 5,558,094 A | 9/1996 | Quay | 128/662.02 |
| 5,558,853 A | 9/1996 | Quay | 424/9.5 |
| 5,558,854 A | 9/1996 | Quay | 424/9.52 |
| 5,558,855 A | 9/1996 | Quay | 424/9.5 |
| 5,558,856 A | 9/1996 | Klaveness et al. | 424/9.37 |
| 5,560,364 A | 10/1996 | Porter | 128/662.02 |
| 5,562,608 A | 10/1996 | Sekins et al. | 604/20 |
| 5,562,893 A | 10/1996 | Lohrmann | 424/9.52 |
| 5,565,215 A | 10/1996 | Gref et al. | 424/501 |
| 5,567,413 A | 10/1996 | Klaveness et al. | 424/9.52 |
| 5,567,414 A | 10/1996 | Schneider et al. | 424/9.52 |
| 5,567,765 A | 10/1996 | Moore et al. | 524/801 |
| 5,569,448 A | 10/1996 | Wong et al. | 424/9.45 |
| 5,569,449 A | 10/1996 | Klaveness et al. | 424/9.51 |
| 5,571,797 A | 11/1996 | Ohno et al. | 514/44 |
| 5,573,751 A | 11/1996 | Quay | 424/9.52 |
| 5,578,292 A | 11/1996 | Schneider et al. | 424/9.51 |
| 5,585,112 A | 12/1996 | Unger et al. | 424/450 |
| 5,593,680 A | 1/1997 | Bara et al. | 424/401 |
| 5,595,723 A | 1/1997 | Quay | 424/9.5 |
| 5,605,673 A | 2/1997 | Schutt et al. | 424/9.51 |
| 5,606,973 A | 3/1997 | Lambert et al. | 128/662.02 |
| 5,612,057 A | 3/1997 | Lanza et al. | 424/450 |
| 5,612,318 A | 3/1997 | Weichselbaum et al. | 514/44 |
| 5,614,169 A | 3/1997 | Klaveness et al. | 424/9.52 |
| 5,620,689 A | 4/1997 | Allen et al. | 424/178.1 |
| 5,626,833 A | 5/1997 | Schutt et al. | 424/9.52 |
| 5,639,443 A | 6/1997 | Schutt et al. | 424/9.52 |
| 5,643,553 A | 7/1997 | Schneider et al. | 424/9.52 |
| 5,648,095 A | 7/1997 | Illum et al. | 424/489 |
| 5,672,585 A | 9/1997 | Pierschbacher et al. | 514/11 |
| 5,676,928 A | 10/1997 | Klaveness et al. | 424/9.32 |
| 5,679,459 A | 10/1997 | Riess et al. | 428/402.2 |
| 5,686,060 A | 11/1997 | Schneider et al. | 424/9.52 |
| 5,686,102 A | 11/1997 | Gross et al. | 424/450 |
| 5,707,352 A | 1/1998 | Sekins et al. | 604/56 |
| 5,707,606 A | 1/1998 | Quay | 424/9.52 |
| 5,707,607 A | 1/1998 | Quay | 424/9.52 |
| 5,711,933 A | 1/1998 | Bichon et al. | 424/9.52 |
| 5,716,597 A | 2/1998 | Lohrmann et al. | 424/9.5 |
| 5,732,707 A | 3/1998 | Widder et al. | 128/661.08 |
| 5,733,527 A | 3/1998 | Schutt | 424/9.52 |
| 5,740,807 A | 4/1998 | Porter | 128/662.02 |
| 5,804,162 A | 9/1998 | Kabalnov et al. | 424/9.51 |
| 5,840,023 A | 11/1998 | Oraevsky et al. | 600/407 |
| 5,855,865 A | 1/1999 | Lambert et al. | 424/9.52 |
| 5,858,399 A | 1/1999 | Lanza et al. | 424/450 |

FOREIGN PATENT DOCUMENTS

| | | |
|---|---|---|
| WO | WO 91/12823 | 9/1991 |
| WO | WO 91/15244 | 10/1991 |
| WO | WO 92/10166 | 6/1992 |
| WO | WO 92/11873 | 7/1992 |
| WO | WO 92/15284 | 9/1992 |
| WO | WO 92/17212 | 10/1992 |
| WO | WO 92/17213 | 10/1992 |
| WO | WO 92/17436 | 10/1992 |
| WO | WO 92/17514 | 10/1992 |
| WO | WO 92/21382 | 10/1992 |
| WO | WO 92/22249 | 12/1992 |
| WO | WO 92/22298 | 12/1992 |
| WO | WO 93/00933 | 1/1993 |
| WO | WO 93/05819 | 1/1993 |
| WO | WO 93/06869 | 4/1993 |
| WO | WO 93/13809 | 7/1993 |
| WO | WO 93/17718 | 9/1993 |
| WO | WO 93/20802 | 10/1993 |
| WO | WO 94/00110 | 1/1994 |
| WO | WO 94/06477 | 3/1994 |
| WO | WO 94/07539 | 4/1994 |
| WO | WO 94/09829 | 5/1994 |
| WO | WO 84/02909 | 8/1994 |
| WO | WO 94/16739 | 8/1994 |
| WO | WO 94/21302 | 9/1994 |
| WO | WO 94/28780 | 12/1994 |
| WO | WO 94/28873 | 12/1994 |
| WO | WO 95/06518 | 3/1995 |
| WO | WO 95/07072 | 3/1995 |
| WO | WO 95/23615 | 9/1995 |
| WO | WO 95/24184 | 9/1995 |
| WO | WO 96/04018 | 2/1996 |
| WO | WO 96/09793 | 4/1996 |
| WO | WO 96/36286 | 11/1996 |
| WO | WO 96/40281 | 12/1996 |
| WO | WO 98/00172 | 1/1998 |

OTHER PUBLICATIONS

Lindner et al., "Myocardial Perfusion Characteristics and Hemodynamic Profile of MRX–115, a Venous Echocardiographic Contrast Agent, During Acute Myocardial Infarction", *J. Am. Soc. Echocardiography,* 1998, 11(1), 36–46.

Regen et al., "Polymerized Phosphatidylcholine Vesicles. Synthesis and Characterization", *J. Am. Chem. Soc.,* 1982, 104(3), 191–195.

Wei et al., "Quantification of Myocardial Blood Flow with Ultrasound–Induced Destruction of Microbubbles Administered as a Constant Venous Infusion", *Circulation,* 1998, 97, 473–483.

Lejbkowicz et al., "The response of normal and malignant cells to ultrasound in vitro", Database *BIOSIS,* No. 1993:95122245 (abstract only).

Jackson et al., "Effect of ultrasound therapy on the repair of Achilles tendon injuries in rats", *Med. Sci. Sports Exercise,* 1991, 23(2), 171–176.

Maxwell, "Therapeutic Ultrasound: Its Effects on the Cellular and Molecular Mechanisms of Inflammation and Repair", *Physiotherapy,* 1992, 78(6), 421–426.

Tuncay et al., "Expression of Genes Associated with Tissue Remodeling Upon Ultrasound Perturbation in the Gingival Fibroblast", *J. Dental Res.,* 1996, 75, 143, (abstract only).

Wang et al., "Low Intensity Ultrasound Treatment Increases Strength in a Rat Femoral Fracture Model", *J. Orthopaedic Res.,* 1994, 12(1), 40–47.

Yang et al., "Exposure to Low–Intensity Ultrasound Increases Aggrecan Gene Expression in a Rat Femur Facture Model", *J. Orthopaedic Res.,* 1996, 14(5), 802–809.

Young et al., "Effect of therapeutic ultrasound on the healing of full–thickness excised skin lesions", *Ultrasonics,* 1990, 28(3), 175–180.

Young et al., "The Effect of Therapeutic Ultrasound on Angiogenesis", *Ultrasound Med. Biol.,* 1990, 16(3), 261–269.

Hynynen et al., "The Usefulness of a Contrast Agent and Gradient Recalled Acquisition in a Steady–State Imaging Sequence for Magnetic Resonance Imaging–Guided Noninvasive Ultrasound Surgery", *Investigative Radiology,* 1994, 29(10), 897–903.

Fitzpatrick, et al., "Metal Ion Catalyzed Decarboxylation: Kinetics and Mechanism of the Oxidative Decarboxylation of Copper (II) Complexes of Aminomalonic Acid in Aqueous Solution", *Inorganic Chemistry,* vol. 13, No. 3, pp. 568–574 (1974).

Thanassi, "Aminomalonic Acid: Spontaneous Decarboxylation and Reaction with 5–Deoxypyridoxal", *Biochemistry,* vol. 9, No. 3, pp. 525–532 (1970).

Stelmashok et al., *Koordinatsionnaya Khimiya,* vol. 3, No. 4, pp. 524–527 (1977) (Russian and English language versions).

Mayhew et al., "High–Pressure Continuous–Flow System for Drug Entrapment in Liposomes", *Methods in Enzymology,* vol. 149, pp. 64–77 (1987).

Mayhew et al., "Characterization of Liposomes Prepared Using a Microemulsifier", *Biochimica et Biophysica Acta,* vol. 775, pp. 169–174 (1984).

Hope et al.,"Production of Large Unilamellar Vesicles by a Rapid Extrusion Procedure: Characterization of Size Distribution, Trapped Volume, and Ability to Maintain a Membrane Potential", *Biochimica et Biophysica Acta,* 812: 55–65 (1985).

Mayer et al., "Vesicles of Variable Size Produced by a Rapid Extrusion Procedure", *Biochimica et Biophysica Acta,* vol. 858, pp. 161–168 (1986).

Cheng, et al., "The Production and Evaluation of Contrast–Carrying Liposomes Made with an Automatic High Pressure System", *Investigative Radiology,* vol. 22, pp. 47–55 (1987).

Jain, et al., *Introduction to Biological Membranes,* Ch. 9, pp. 192–231 (J. Wiley and Sons, N.Y. 1980).

Sigel, H., ed., *Metal Ions in Biological Systems: Antibiotics and Their Complexes,* vol. 19 (Marcel Dekker, N.Y. 1985).

Nayar et al., "Generation of Large Unilamellar Vesicles From Long–chain Saturated Phosphatidylcholines by Extrusion Technique", *Biochimica et Biophysica Acta,* vol. 986, pp. 200–206 (1989).

Hope et al., "Generation of Multilamellar and Unilamellar Phospholipid Vesicles", *Chemistry and Physics of Lipids,* vol. 40, pp. 89–107 (1986).

Mattrey et al., "Perfluorochemicals as US Contrast Agents for Tumor–Imaging and Hepatosplenography: Preliminary Clinical Results", *Radiology,* vol. 163, pp. 339–343 (1987).

Mattrey et al., "Perfluoroctylbromide: A Liver/Spleen–Specific and Tumor Imaging Ultrasound Contrast Material", *Radiology,* vol. 145, pp. 759–762 (1982).

Keller et al., "Successful Left Ventricular Opacification Following Peripheral Venous Injection of Sonicated Contrast Agent: An Experimental Evaluation", *LV Contrast Echocardiography,* vol. 114, No. 3, pp. 570–575 (1987).

Feinstein et al., "Two–Dimensional Contrast Echocardiography, I: In Vitro Development and Quantitative Analysis of Echo Contrast Agents", *JACC,* vol. 3, No. 1, pp. 14–20 (1984).

Ten Cate et al., "Two–Dimensional Contrast Echocardiography, II: Transpulmonary Studies", *JACC,* vol. 3, No. 1, pp. 21–27 (1984).

Unger et al., "Hepatic Metastases: Liposomal Gd–DTPA–enhanced MR Imaging", *Radiology,* vol. 171, pp. 81–85 (1989).

Deamer et al., "Permeability of Lipid Bilayers to Water and Ionic Solutes", *Chemistry and Physics of Lipids,* vol. 40, pp. 167–188 (1986).

Gutknecht et al., "Diffusion of Carbon Dioxide Through Lipid Bilayer Membranes: Effect of Carbonic Anhydrase, Bicarbonate, and Unstirred Layers", *Chemical Abstracts,* 87:34772q (1977).

Scarpa et al., "Cation Permeability of Liposomes as a Function of the Chemical Composition of the Lipid Bilayers", *Biochimica et Biophysica Acta,* vol. 241, pp. 789–797 (1971).

MacNaughton et al., "Effects of Gaseous Anesthetics and Inert Gases on the Phase Transition in Smectic Mesophases of Dipalmitoyl Phosphatidylcholine", *Biochimica et Biophysica Acta,* vol. 597, pp. 193–198 (1980).

Tilcock et al., "Liposomal Gd–DTPA: Preparation and Characterization of Relaxivity", *Radiology,* vol. 171, pp. 77–80 (1989).

Mann et al., "Formation of Iron Oxides in Unilamellar Vesicles", *Journal of Colloid and Interface Science,* vol. 122, No. 2, pp. 326–335 (1988).

Anderson et al., "Manganese (III) Complexes in Oxidative Decarboxylation of Acids", *J. Am. Chem. Soc.,* vol. 92, No. 8, pp. 2450–2460 (1970).

Muhlradt et al., "Vitamin B6 Analogs: An Improved Synthesis of 5–Deoxypyridoxal", *New Compounds,* vol. 10, pp. 129–130 (1967).

Chapman D., "Physiochemical Properties of Phospholipids and Lipid Water Systems", *Liposome Technology,* Gregoriadis, G., ed., vol. 1, pp. 1–18 (CRC Press, Boca Raton, FL, 1984).

Violante et al., "Particulate Suspensions as Ultrasonic Contrast Agents for Liver and Spleen", *Inv. Rad.,* vol. 23, pp. S294–S297, Sep. 1988.

Fritzsch et al., "Preclinical and Clinical Results with an Ultrasonic Contrast Agent", *Inv. Rad.,* vol. 23, pp. S302–S305, Sep. 1988.

Brochure, *Experience,* Sonicator™, Heat Systems–Ultrasonics, Inc. (1987).

M. Ostro, "Liposomes", Marcel Dekker, New York, pp. 102–103 (1983).

Fukuda et al., "Polymer–Encased Vesicles Derived from Diotadecyldimethylammonium Methacrylate", *J. Am. Chem. Soc.*, vol. 108, pp. 2321–2327 (1986).

Regen, "Polymerizaed Vesicles", *J. Am. Chem. Soc.*, vol. 102, pp. 6638–6640 (1989).

Rose, A. and Rose, E., "The Condensed Chemical Dictionary", Reinhold Publishing, New York, pp. 728 and 743 (1966).

A.G. Belykh, *Farmakol Toksikol. (MOSC)*, vol. 44(3), pp. 322–326 (1981) (abstract).

J. Vion–Dury et al., *J. Pharmacol. Exper. Ther.*, vol. 250(3), pp. 1113–1118 (1989) (abstract).

M.R. Zalutsky et al., *Invest. Radiol.*, vol. 22(2), pp. 141–147 (1987) (abstract).

Crowe et al., *Archives of Biochemistry and Biophysics*, vol. 242, pp. 240–247 (1985).

Crowe et al., *Archives of Biochemistry and Biophysics*, vol. 220, pp. 477–484 (1983).

Dorland's Illustrated Medical Dictionary, p. 946, 27th ed. (W.B. Saunders Company, Philadelphia 1988).

*Liposome Technology*, Gregoriadis, G., ed., vol. I, pp. 30–35, 51–65 and 79–107 (CRC Press Inc., Boca Raton, FL, (1984).

Madden et al., *Chemistry and Physics of Lipids*, vol. 53, pp. 37–46 (1990).

Sinkula et al., *J. Pharm. Sci.*, vol. 64, pp. 181–210 (1975).

Shiina et al., "Hyperthermiably Low–frequency Synthesized Ultrasound", *IEEE Engineering*, pp. 879–880, vol. 2 (1988) (abstract).

McAvoy et al., *IEEE Engineering, Ultrasonics Symposium Proceedings*, vol. 2, pp. 677–1248 (1989) (abstract).

Chapman et al., "Biomembrane Phase Transitions", *J. Biol. Chem.*, 1974, 249:2512–2521.

Hug et al., "Liposomes for the Transformation of Eukaryotic Cells", *Biochimica et Biophysica Acta*, 1991, 1097:1–17.

Marsh, *CRC Handbook of Lipid Bilayers* (CRC Press, Boca Raton, FL 1990) pp. 139–141.

Szoka et al., "Procedure for Preparation of Liposomes with Large Internal Aqueous Space . . . ", *Proc. Natl. Acad. Sci.* 1978, 75:4194–4198.

Acoustic Imaging; AI5200; Convex Curved Linear Array Ultrasound Transducers Operator's Manual, Nov. 20, 1989, 4700–0003–1C, p. 4.

Bangham et al., "Diffusion of Univalent Ions across the Lamellae of Swollen Phospholipids", *J. Mol. Biol.*, 1965, 13:238–252.

Carson et al., *Ultrasound in Med. & Biol.* 3, 1978, 341–350.

Kost et al., *Polymers in Medicine II: Biomedical and Pharmaceutical Applications*, "Ultrasonic Modulated Drug Delivery Systems", Chiellini et al., ed., (Plenum Press, New York and London), pp. 387–396 (1985).

deGier et al., "Relations Between Liposomes and Biomembranes", *Annals of The New York Academy of Sciences*, 1978, 308:85–99.

Felgner et al., "Lipofection: A highly efficient, lipid–mediated DNA–transfection procedure", *Proc. Natl. Acad. Sci.*, 1987, 84:7413–7417.

Gabizon et al., "Liposome formulations with prolonged circulation time in blood and enhanced uptake by tumors", *Proc. Natl. Acad. Sci.*, 1988, 85:6949–6953.

Garelli, et al., *Biochimica et Biophysica Acta*, vol. 1127:41–48 (1992).

Kawai et al., "New Procedure for DNA Transfection with Polycation and Dimethyl Sulfoxide", *Molecular and Cellular Biology*, 1984, 4:1172–1174.

Kuo et al., "Metallocene Antitumor Agents. Solution and Solid–State Molybdenocene Coordination . . . ", *J. Am. Chem. Soc.*, 1991, 113:9027–9045.

MacDonald, *Mammalian Cell Biotechnology: A Practical Approach*, M. Butler, ed., 1991 (Oxford University Press, New York), p. 57–70.

Mathiowitz et al., "Photochemical Rupture of Microcapsules: A Model System", *Journal of Applied Polymer Science*, 1981, 27:809–822.

May et al., "Cationic Liposomes Enable Bovine Herpesvirus Type 2 DNA to Infect Cells", *Acta virol.*, 1991, 35:107.

Poznansky et al., "Biological Approaches to the Controlled Delivery of Drugs: A Critical Review", *Pharmacol, Rev.*, 1984, 36:277–336.

Sato et al., "Recent Aspects in the Use of Liposomes in Biotechnology and Medicine", *Prog. Lipid Res.* 1992, 4:345–372.

Simons et al., "Antisense c–myb oligonucleotides inhibit intimal arterial smooth muscle cell accumulation in vivo", *Nature*, 1992, 359:67–70.

Thompson, Larry, "At Age 2, Gene Therapy Enters a Growth Phase", *Science* 1992, 258:744–746.

Trubetskoy et al. "Cationic liposomes enhance targeted delivery and expression of exogenous DNA . . . ", *Biochimica et Biophysica Acta* 1992, 131:311–313.

Umemura et al., "Studies on Sonodynamic Cancer Therapy", *IEEE*, 1992, O–7803–0785, pp. 354–355.

Williams, "Human Gene Therapy: Searching for Better Vectors", *ASM News* [American Society for Microbiology] 1992, 58:67–69.

Woodle et al., "Versatility in lipid compositions showing prolonged circulation . . . ", *Biochimica et Biophysica Acta* 1992, 1105:193–200.

Zhou et al., "Targeted delivery of DNA by liposomes and polymers", *J. of Controlled Release* 1992, 19:269–274.

Mathiowitz et al., "Polyanhydride Microspheres as Drug Carriers", *Journal of Applied Polymer Science*, vol. 35, pp. 755–774 (1988).

Sankaram et al., "Cholesterol–Induced Fluid–Phase Immiscibility in Membranes", *Proc. Natl. Acad. Sci.*, vol. 88, pp. 8686–8690 (1991).

*Scientific Apparatus Catalog 92/93* (VWR Scientific, 1991), "Syringes", pp. 1511–1513; "Filtration, Syringe Filters", pp. 766–768; "Filtration, Membranes", pp. 750–753; "Filtration, Filter Holders", p. 744.

Gramiak et al., *Radiology*, "Detection of Intracardiac Blood Flow by Pulsed Echo–Ranging", pp. 415–418 (1971).

Feigenbaum et al., *Circulation*, "Identification of Ultrasound Echoes from the Left Ventricle by Use of Intracardiac Injections of Indocyanine Green", vol. XL1, pp. 615–631 (1970).

Santaella, et al., *FEBS 13463*, "Extended In Vivo Blood Circulation Time of Fluorinated Liposomes", vol. 336, No. 3, pp. 481–484 (1993).

Brown and Langer, *Annual Review Medicine*, 1988, 39:221 29, Annual Review, Inc., "Transdermal Delivery of Drugs", pp. 221–229.

Moseley, et al., *Microbubbles: A Novel MR Susceptibility Contrast Agent*, abstract, 1991 Napa, California Meeting of the Society for Magnetic Resonance in Medicine.

Ter–Pogossian *Tomography*, Kee, et al., n, "Physical Principles and Instrumentation", *Computed Body* eds., Raven Press, New York, Chapter 1, pp. 1–7 (1988).

Aronberg, "Techniques", *Computed Body Tomography*, Kee, et al., eds., Raven Press, New York, Chapter 2, pp. 9–36 (1988).

Miller, *Ultrasonics* (Sep. 1981), "Ultrasonic detection of resonant cavitation bubbles in a flow tube by their second–harmonic emissions," pp. 217–224.

Dittrich, "Cardiac Muscle Ischemia and Infarction", *The Second Annual International Symposium on Contrast Agents in Diagnostic Ultrasound*, Atlantic City, NJ (May 7, 1996) (abstract).

Pantely, "Intravenous Contrast Echocardiography–Tissue Imaging & Quantification of Coronary Blood Flow", *The Second Annual International Symposium on Contrast Agents in Diagnostic Ultrasound*, Atlantic City, NJ (May 7, 1996) (abstract).

Schutt et al., "Osmotically Stabilized Microbubble Sonographic Contrast Agents", *Acad. Radiol.*, vol. 3, Suppl. 2, pp. S188–S190 (Aug. 1996).

Frézard, et al., "Permeability and stability in buffer and in human serum of fluorinated phospholipid–based liposomes", *Biochimica et Biophysica Acta*, 1192, pp. 61–70 (1994).

Frézard, et al., "Fluorinated Phospholipid–Based Vesicles as Potential Drug Carriers: Encapsulation/Sustaining of Drugs and Stability in Human Serum", *Art, Cells, Blood Subs., and Immob. Biotech.*, 22(4), pp. 1403–1408 (1994).

Chang et al., "Semipermeable Aqueous Microcapsules", *Canadian J. Of Phys. And Pharm.*, 1966, 44, 115–128.

Chang, "Semipermeable Microcapsules", *Science*, 1964, 146, 524–525.

Deasy, *Microencapsulation and Related Drug Processes*, 1983, vol. 20, Chs. 9 and 10, 195–240 (Marcel Dekker, Inc., NY).

Yeung et al., "Preparation of Microencapsulated Liposomes", *J. Microencapsulation*, 1988, 5, 331–337.

Mattrey et al., Gas Emulsions as Ultrasound Contrast Agents; Preliminary Results in Rabbits and Dogs, *Investigative Radiology*, vol. 29, Jun. Supp. 2, pp. S139–S141, 1994.

Meltzer et al., Transmission of Ultrasonic Contrast Through the Lungs, *Ultrasound in Med. & Biol.*, vol. 7, No. 4, 377–384, 1981.

PR Newswire, Apr. 1, 1986.

Swanson et al., Chapter 22, "Enhancement Agents for Ultrasound: Fundamentals", *Pharmaceuticals in Medical Imaging*, pp. 682–687 (1990).

Ophir et al., "Contrast Agents in Diagnostic Ultrasound", *Ultrasound in Med. & Biol.*, vol. 15, No. 4, pp. 319–333 (1989).

Jacobs, "Intraocular gas measurement using A–scan ultrasound", *Current Eye Research*, vol. 5, No. 8, pp. 575–578 (1986).

Lincoff et al., "Intravitreal Expansion of Perfluorocarbon Bubbles", *Arch. Ophthalmol.*, vol. 98, p. 1646, Sep. 1980.

Lincoff et al., "Intravitreal Longevity of Three Perfluorocarbon Gases", *Arch. Ophthalmol.*, vol. 98, pp. 1610–1611, Sep. 1980.

Lincoff et al., "The Perfluorocarbon Gases in the Treatment of Retinal Detachment", *Ophthalmology*, vol. 90, No. 5, pp. 546–551, May 1983.

Gardner et al., "A Survey of Intraocular Gas Use in North America", *Arch. Ophthalmol.*, vol. 106, pp. 1188–1189, Sep. 1988.

Unger et al., "Liposomal MR Contrast Agents", *J. Liposome Research*, 4(2), pp. 811–834 (1994).

Feinstein, Steven B., "Myocardial Perfusion Imaging: Contrast Echocardiography Today and Tomorrow," *Journal of the American College of Cardiology*, 8(1):251–253 (1986).

Keller et al., "The Behavior of Sonicated Albumin Microbubbles Within the Microcirulation: A Basis for Their Use During Myocardial Contrast Echocardiography", *Circulation Res.*, 65(2):458–465 (1989).

Lincoff et al., "Perfluoro–n–butane: A Gas for Maximum Duration Retinal Tamponade," *Arch Ophthalmology*, 101:460–462 (1983).

*Remington's Pharmaceutical Sciences*, John Hoover, managing ed., Mack Publishing Company, Easton, PA, pp. 295–298; 736; 1242–1244 (1975).

*Handbook of Pharmaceutical Excipients*, American Pharmaceutical Association, Washington, D.C. and The Pharmaceutical Society of Great Britain, London, England, pp. 181–183 (1986).

Barnhart et al., "Characteristics of Albunex™: Air–Filled Microspheres for Echocardiography Contrast Enhancement," *Investigative Radiology*, 25:S162–164 (1990).

Levene et al., "Characterization of Albunex™," *J. Acoust. Soc. Am.*, 87(Suppl. 1):569–70 (1990).

Miller et al., "Physiochemical Approaches to the Mode of Action of General Anesthetics," *J. Amer. Soc. Anesthesiologists*, 36(4):339–351 (1972).

"Properties and Applications of the 'Freon' Fluorocarbons" in DuPont Freon Technical Bulletin B–2 (E.I. DuPont de Nemours and Company, Wilmington, DE), pp. 1–11 (1964).

"'Freon' Fluorocarbons: Properties and Applications" in DuPont Technical Bulletin G–1 (E.I. DuPont de Nemours and Company, Wilmington, DE), pp. 1–10 (1987).

"Encyclopedia of Polymer Sciences and Engineering," John Wiley & Sons, New York, 1:164–169 (1985).

"Concise Encyclopedia of Polymer Science and Engineering," J. Kroschwitz, ed., John Wiley & Sons, New York, pp. 12–13 (1990).

Wheatley et al., "Contrast Agents for Diagnostic Ultrasound: Development and Evaluation of Polymer–Coated Microbubbles," *Biomaterials*, 11:713–717 (1990).

Villanueva et al., "Characterization of Spatial Patters of Flow Within the Reperfused Myocardium by Myocardial Contrast Echocardiography", *Circulation*, vol. 88, No. 6, pp. 2596–2606 (Dec. 1993).

Desir et al., "Assessment of regional myocardial perfusion with myocardial contrast echocardiography in a canine model of varying degrees of coronary stenosis", *American Heart Journal*, vol. 127, No. 1, pp. 56–63 (Jan. 1994).

Sekins et al., "Lung Cancer Hyperthermia via Ultrasound and PFC Liquids", *Published in Proceedings of 5th International Symposium on Hyperthermic Oncology, Kyoto, Japan*, (3 pages) (Aug. 29–Sep. 3, 1998).

Pietersen, "A New Warning System for Fires of Electrical Origin", *CERN European Organization for Nuclear Research, Health and Safety Division*, pp. 1–5 (Mar. 1977).

Reexamination of U.S. Patent No. 5,527,521, Reexam Control No. 90/004,719.

Reexamination of U.S. Patent No. 5,547,656, Reexam Control No. 90/004,720.

* cited by examiner

CONTAINER WITH MULTI-PHASE COMPOSITION FOR USE IN DIAGNOSTIC AND THERAPEUTIC APPLICATIONS

RELATED APPLICATIONS

This application is a divisional of application U.S. Ser. No. 08/741,598, filed Nov. 1, 1996, which is a divisional of application U.S. Ser. No. 08/307,305, filed on Sep. 16, 1994, which is a continuation-in-part of application U.S. Ser. No. 08/159,687, filed Nov. 30, 1993, now U.S. Pat. No. 5,585,112, which in turn is a continuation-in-part of application U.S. Ser. No. 08/076,239, filed Jun. 11, 1993, now U.S. Pat. No. 5,469,854, which in turn is a continuation-in-part of application U.S. Ser. No. 07/717,084, filed Jun. 18, 1991, now U.S. Pat. No. 5,228,446, and application U.S. Ser. No. 07/716,899, filed Jun. 18, 1991, now abandoned which in turn are continuation-in-part of application U.S. Ser. No. 07/569,828, filed Aug. 20, 1990 now U.S. Pat. No. 5,088,499, which in turn is a continuation-in-part of application U.S. Ser. No. 07/455,707, filed Dec. 22, 1989, now abandoned The Ser. No. 08/307,305 application is also a continuation-in-part of application U.S. Ser. No. 08/160,232, filed Nov. 30, 1993, now U.S. Pat. No. 5,542,935, which in turn is a continuation-in-part of application U.S. Ser. No. 08/076,250, filed Jun. 11, 1993 now U.S. Pat. No. 5,580,575, which in turn is a continuation-in-part of application U.S. Ser. No. 07/717,084, filed Jun. 18, 1991, now U.S. Pat. No. 5,228,446, and application U.S. Ser. No. 07/716,899, filed Jun. 18, 1991, now abandoned which in turn are continuation-in-part of application U.S. Ser. No. 07/569,828, filed Aug. 20, 1990 now U.S. Pat. No. 5,088,499, which in turn is a continuation-in-part of application U.S. Ser. No. 07/455,707, filed Dec. 22, 1989, now abandoned.

The Ser. No. 08/307,305 application is further a continuation-in-part of application U.S. Ser. No. 08/212,553, filed Mar. 11, 1994, now abandoned, which in turn is a continuation-in-part of application U.S. Ser. No. 08/076,239 and application U.S. Ser. No. 08/076,250, both of which were filed Jun. 11, 1993. The parentage of applications U.S. Ser. Nos. 076,239 and 076,250 is set forth above.

Priority to each of these applications is hereby claimed, and the disclosures of each are hereby incorporated herein by reference in their entirety.

BACKGROUND OF THE INVENTION

Ultrasound is a diagnostic imaging technique which provides a number of significant advantages over other diagnostic methodology. Unlike imaging techniques such as nuclear medicine and X-rays, ultrasound does not expose the patient to the harmful effects of ionizing radiation. Moreover, ultrasound is relatively-inexpensive and can be conducted as a portable examination.

In ultrasound imaging, sound is transmitted into a patient or animal via a transducer. When the sound waves propagate through the body, they encounter interfaces from tissues and fluids. Depending on the acoustic properties of the tissues and fluids in the body, the ultrasound sound waves are partially or wholly reflected or absorbed. When sound waves are reflected by an interface they are detected by the receiver in the transducer and processed to form an image. The acoustic properties of the tissues and fluids within the body determine the contrast which appears in the resultant image.

Magnetic resonance imaging (MRI) is a relatively new imaging technique which, unlike X-rays, does not utilize ionizing radiation. Like computed tomography, MRI can make cross-sectional images of the body, however MRI has the additional advantage of being able to make images in any scan plane (i.e., axial, coronal, sagittal or orthogonal).

MRI employs a magnetic field, radiofrequency energy and magnetic field gradients to make images of the body. The contrast or signal intensity differences between tissues mainly reflect the T1 and T2 relaxation values and the proton density (effectively, the free water content) of the tissues.

Advances have been made in recent years in diagnostic ultrasound and MRI technology. However, despite the various technological improvements, ultrasound and MRI are still imperfect tools in a number of respects, particularly with regard to the imaging and detection of disease in the liver and spleen, kidneys, heart and vasculature, including the measurement of blood flow. The ability to detect these regions and make such measurements depends on the difference in acoustic properties (ultrasound) or T1 and T2 signal intensity (MRI) between tissues or fluids and the surrounding tissues or fluids. Accordingly, contrast agents which will increase these differences between tissues or fluids and the surrounding tissues or fluids, and improve ultrasonic or magnetic resonance imaging and disease detection, have been sought. As a result of this effort, new and better contrast agents have been developed. Nonetheless, one recurrent problem with many of such contrast agents has been shelf-life stability, making long term storage a problem.

The present invention addresses these and other concerns by providing a convenient container comprising an aqueous lipid suspension phase and a gaseous phase substantially separate from the aqueous lipid suspension phase which, upon agitation prior to use, produces an excellent gas-filled liposome contrast agent for use in such applications as ultrasound or magnetic resonance imaging, as well as other uses. Since the contrast agent is prepared immediately prior to use, shelf-life stability problems are avoided.

SUMMARY OF THE INVENTION

The present invention provides a container comprising (i) an aqueous lipid suspension phase and (ii) a gaseous phase substantially separate from the aqueous lipid suspension phase. Prior to use, the contents of the container may be agitated, thereby producing a gas-filled liposome composition having excellent utility as a contrast agent for use, for example, in ultrasonic or magnetic resonance imaging, as well as in therapeutic applications. The ability in accordance with the present invention to prepare the contrast agent immediately prior to use avoids problems of shelf-life stability experienced with many prior art contrast agents. The self-contained unit of the invention also allows for easy sterilization.

These and other aspects and advantages of the present invention are discussed in greater detail below.

DETAILED DESCRIPTION OF THE INVENTION

Figure 1:
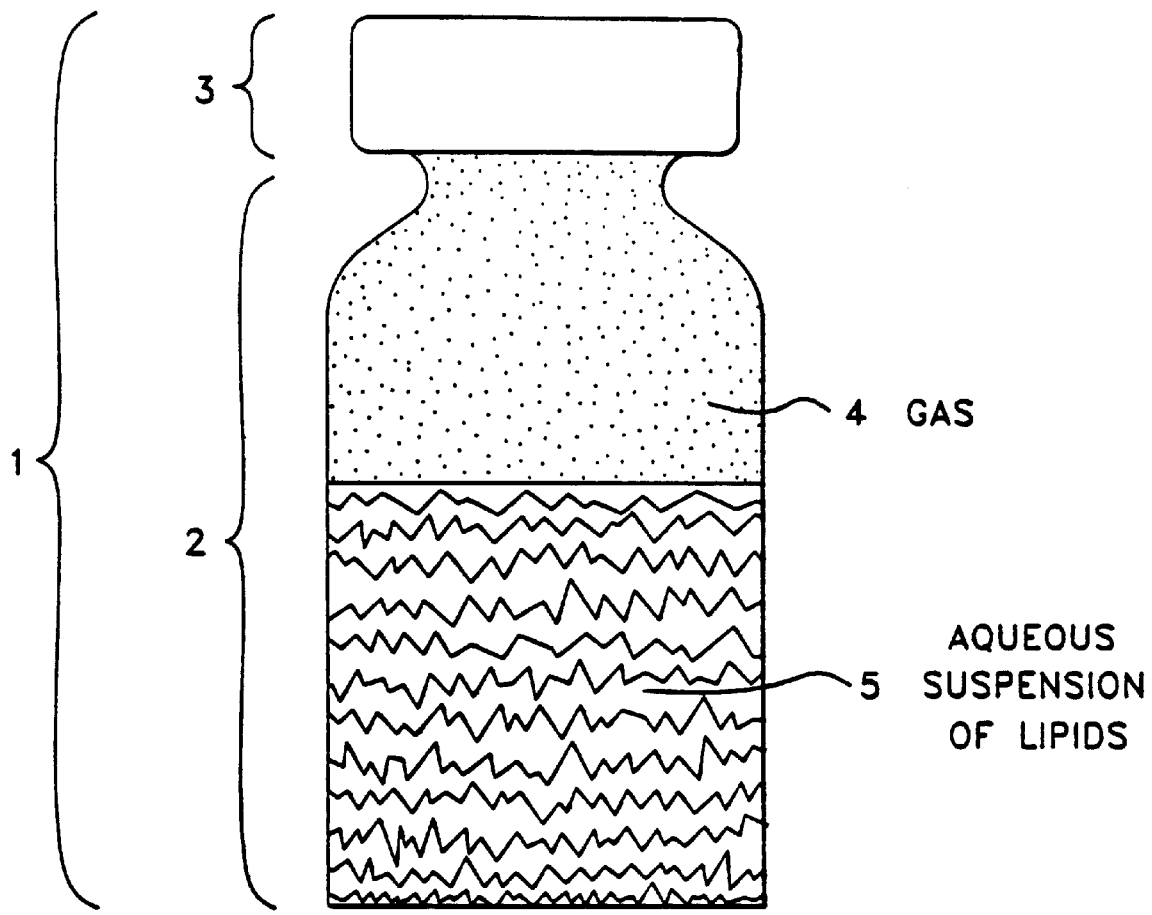
FIG. 1 is a side cross-sectional view of a container filled with an aqueous suspension of lipids and a substantially separate headspace of gas.

The container of the present invention comprises an aqueous lipid suspension phase and a substantially separate gaseous phase. Prior to use, the container and its contents may be agitated, causing the lipid and gas phases to mix, resulting in the formation of gas-filled liposomes which entrap the gas. The resulting gas-filled liposomes provide an excellent contrast enhancement agent for diagnostic imaging, particularly using ultrasound or magnetic resonance imaging.

A wide variety of lipids may be employed in the aqueous lipid suspension phase. The lipids may be saturated or unsaturated, and may be in linear or branched form, as desired. Such lipids may comprise, for example, fatty acids molecules that contain a wide range of carbon atoms, preferably between about 12 carbon atoms and about 22 carbon atoms. Hydrocarbon groups consisting of isoprenoid units, prenyl groups, and/or sterol moieties (e.g., cholesterol, cholesterol sulfate, and analogs thereof) may be employed as well. The lipids may also bear polymer chains, such as the amphipathic polymers polyethyleneglycol (PEG) or polyvinylpyrrolidone (PVP) or derivatives thereof (for in vivo targeting), or charged amino acids such as polylysine or polyarginine (for binding of a negatively charged compound), or carbohydrates (for in vivo targeting) such as is described in U.S. Pat. No. 4,310,505, or glycolipids (for in vivo targeting), or antibodies and other peptides and proteins (for in vivo targeting), etc., as desired. Such targeting or binding compounds may be simply added to the aqueous lipid suspension phase or may be specifically chemically attached to the lipids. The lipids may also be anionic or cationic lipids, if desired, so that they may themselves be capable of binding other compounds such as pharmaceuticals, genetic material, or other therapeutics.

Examples of classes of suitable lipids and specific suitable lipids include: phosphatidylcholines, such as dioleoylphosphatidylcholine, dimyristoylphosphatidylcholine, dipalmitoylphosphatidylcholine (DPPC), and distearoyl-phosphatidylcholine; phosphatidylethanolamines, such as dipalmitoylphosphatidylethanolamine (DPPE), dioleoyl-phosphatidylethanolamine and N-succinyl-dioleoyl-phosphatidylethanolamine; phosphatidylserines; phosphatidylglycerols; sphingolipids; glycolipids, such as ganglioside GM1; glucolipids; sulfatides; glycosphingolipids; phosphatidic acids, such as dipalmatoylphosphatidic acid (DPPA); palmitic fatty acids; stearic fatty acids; arachidonic fatty acids; lauric fatty acids; myristic fatty acids; lauroleic fatty acids; physeteric fatty acids; myristoleic fatty acids; palmitoleic fatty acids; petroselinic fatty acids; oleic fatty acids; isolauric fatty acids; isomyristic fatty acids; isopalmitic fatty acids; isostearic fatty acids; cholesterol and cholesterol derivatives, such as cholesterol hemisuccinate, cholesterol sulfate, and cholesteryl-(4'-trimethylammonio)-butanoate; polyoxyethylene fatty acid esters; polyoxyethylene fatty acid alcohols; polyoxyethylene fatty acid alcohol ethers; polyoxyethylated sorbitan fatty acid esters; glycerol polyethylene glycol oxystearate; glycerol polyethylene glycol ricinoleate; ethoxylated soybean sterols; ethoxylated castor oil; polyoxyethylene-polyoxypropylene fatty acid polymers; polyoxyethylene fatty acid stearates; 12-(((7'-diethylaminocoumarin-3-yl)-carbonyl)-methylamino)-octadecanoic acid; N-[12-(((7'-diethylamino-coumarin-3-yl)-carbonyl)-methyl-amino)octadecanoyl]-2-aminopalmitic acid; 1,2-dioleoyl-sn-glycerol; 1,2-dipalmitoyl-sn-3-succinylglycerol; 1,3-dipalmitoyl-2-succinyl-glycerol; and 1-hexadecyl-2-palmitoyl-glycerophosphoethanolamine and palmitoylhomocysteine; lauryltrimethylammonium bromide (lauryl-=dodecyl-); cetyltrimethylammonium bromide (cetryl-=hexadecyl-); myristyltrimethylammonium bromide (myristyl-=tetradecyl-); alkyldimethylbenzylammonium chlorides, such as wherein alkyl is a $C_{12}$, $C_{14}$ or $C_{16}$ alkyl; benzyldimethyldodecylammonium bromide; benzyldimethyldodecylammonium chloride, benzyldimethylhexadecylammonium bromide; benzyldimethylhexadecylammonium chloride; benzyldimethyltetradecylammonium bromide; benzyldimethyltetradecylammonium chloride; cetyldimethylethylammonium bromide; cetyldimethylethylammonium chloride; cetylpyridinium bromide; cetylpyridinium chloride; N-[1-2,3-dioleoyloxy)-propyl]-N,N,N-trimethylammonium chloride (DOTMA); 1,2-dioleoyloxy-3-(trimethylammonio)propane (DOTAP); and 1,2-dioleoyl-e-(4'-trimethylammonio)-butanoyl-sn-glycerol (DOTB).

As will be apparent to those skilled in the art, once armed with the present disclosures, the foregoing list of lipids is exemplary only, and other useful lipids, fatty acids and derivatives and combinations thereof, may be employed, and such additional compounds are also intended to be within the scope of the term lipid, as used herein. As the skilled artisan will recognize, such lipids and/or combinations thereof may, upon agitation of the container, form liposomes (that is, lipid spheres having an internal void) which entrap gas from the gaseous phase in their internal void. The liposomes may be comprised of a single lipid layer (a lipid monolayer), two lipid layers (a lipid bilayer) or more than two lipid layers (a lipid multilayer).

As a general matter, it is preferred that the lipids remain in the gel state, that is, below the gel state to liquid crystalline state phase transition temperature ($T_m$) of the lipid material, particularly during agitation. Gel state to liquid crystalline state phase transition temperatures of various lipids are well known. Such temperatures may also be readily calculated using well known techniques. Table 1, below, from Derek Marsh, "CRC Handbook of Lipid Bilayers", page 139, CRC Press, Boca Raton, Fla. (1990), shows, for example, the main chain phase transition temperatures for a variety of representative saturated phosphocholine lipids.

TABLE 1

Saturated Diacyl-sn-Glycero-(3)-Phosphocholines:
Main Chain Melting Transitions

| # Carbons in Acyl Chains | Main Phase Transition Temperature °C. |
| --- | --- |
| 1,2-(12:0) | −1.0 |
| 1,2-(13:0) | 13.7 |
| 1,2-(14:0) | 23.5 |
| 1,2-(15:0) | 34.5 |
| 1,2-(16:0) | 41.4 |
| 1,2-(17:0) | 48.2 |
| 1,2-(18:0) | 55.1 |
| 1,2-(19:0) | 61.8 |
| 1,2-(20:0) | 64.5 |
| 1,2-(21:0) | 71.1 |
| 1,2-(22:0) | 74.0 |
| 1,2-(23:0) | 79.5 |
| 1,2-(24:0) | 80.1 |

In a preferred embodiment of the invention, the aqueous lipid phase further comprises a polymer, preferably an amphipathic polymer, and preferably one that is directly bound (i.e., chemically attached) to the lipid. Preferably, the amphipathic polymer is polyethylene glycol or a derivative thereof. The most preferred combination is the lipid dipalmitoylphosphatidylethanolamine (DPPE) bound to polyethylene glycol (PEG), especially PEG of an average molecular weight of about 5000 (DPPE-PEG5000). The PEG or other polymer may be bound to the DPPE or other lipid through a covalent linkage, such as through an amide, carbamate or amine linkage. Alternatively, ester, ether, thioester, thioamide or disulfide (thioester) linkages may be used with the PEG or other polymer to bind the polymer to, for example, cholesterol or other phospholipids. A particularly preferred combination of lipids is DPPC, DPPE-PEG5000 and DPPA, especially in a ratio of about 82%:8%:10% (mole %), DPPC: DPPE-PEG5000:DPPA.

To prepare the aqueous phase, the lipid may be combined with water (preferably distilled water), normal (physiological) saline solution, phosphate buffered saline solution, or other aqueous based solution, as will be apparent to those skilled in the art.

A wide variety of different gases may be employed in the gaseous phase of the present invention. Preferably the gases are substantially insoluble in the aqueous lipid suspension phase. By substantially insoluble, it is meant that the gas maintains a solubility in water at 20° C. and 1 atmosphere of pressure of equal to or less than about 18 ml of gas per kg of water. As such, substantially insoluble gases have a solubility which is less than the solubility of nitrogen gas. Preferably, the solubility is equal to or less than about 15 ml of gas per kg of water, more preferably equal to or less than about 10 ml of gas per kg of water, at 20° C. and 1 atmosphere of pressure. In one preferable class of gases, the solubility is between about 0.001 and about 18 ml of gas per kg of water, or between about 0.01 and about 15 ml of gas per kg of water, or between about 0.1 and about 10 mg of gas per kg of water, or between about 1 and about 8 mg of gas per kg of water, or between about 2 and 6 ml per kg of water, at the aforementioned temperature and pressure. Perfluorocarbon gases and the fluorinated gas sulfur hexafluoride are, for example, less soluble than 10 ml of gas per kg of water, at 20° C. and 1 atmosphere of pressure, and thus are preferred. Gases which are not substantially insoluble, as defined herein, are referred to as soluble gases.

Other suitable substantially insoluble or soluble gases include, but are not limited to, hexafluoroacetone, isopropylacetylene, allene, tetrafluoroallene, boron trifluoride, 1,2-butadiene, 1,3-butadiene, 1,2,3-trichlorobutadiene, 2-fluoro-1,3-butadiene, 2-methyl-1,3 butadiene, hexafluoro-1,3-butadiene, butadiyne, 1-fluorobutane, 2-methylbutane, decafluorobutane (perfluorobutane), decafluoroisobutane (perfluoroisobutane), 1-butene, 2-butene, 2-methy-1-butene, 3-methyl-1-butene, perfluoro-1-butene, perfluoro-1-butene, perfluoro-2-butene, 4-phenyl-3-butene-2-one, 2-methyl-1-butene-3-yne, butylnitrate, 1-butyne, 2-butyne, 2-chloro-1, 1,1,4,4,4-hexafluoro-butyne, 3-methyl-1-butyne, perfluoro-2-butyne, 2-bromo-butyraldehyde, carbonyl sulfide, crotononitrile, cyclobutane, methylcyclobutane, octafluorocyclobutane (perfluorocyclobutane), perfluoroisobutane, 3-chlorocyclopentene, cyclopropane, 1,2-dimethylcyclopropane, 1,1-dimethylcyclopropane, ethyl cyclopropane, methylcyclopropane, diacetylene, 3-ethyl-3-methyldiaziridine, 1,1,1-trifluorodiazoethane, dimethylamine, hexafluorodimethylamine, dimethylethylamine, bis-(dimethyl phosphine)amine, 2,3-dimethyl-2-norbornane, perfluoro-dimethylamine, dimethyloxonium chloride, 1,3-dioxolane-2-one, 1,1,1,1,2-tetrafluoroethane, 1,1,1-trifluoroethane, 1,1,2,2-tetrafluoroethane, 1,1,2-trichloro-1,2,2-trifluoroethane, 1,1-dichloroethane, 1,1-dichloro-1,2,2,2-tetrafluoroethane, 1,2-difluoroethane, 1-chloro-1,1,2,2,2-pentafluoroethane, 2-chloro-1,1-difluoroethane, 1-chloro-1,1,2,2-tetrafluoroethane, 2-chloro-1,1-difluoroethane, chloroethane, chloropentafluoro-ethane, dichlorotrifluoroethane, fluoroethane, nitropentafluoroethane, nitrosopentafluoro-ethane, perfluoroethane, perfluoroethylamine, ethyl vinyl ether, 1,1-dichloroethylene, 1,1-dichloro-1,2-difluoro-ethylene, 1,2-difluoroethylene, methane, methane-sulfonyl-chloride-trifluoro, methane-sulfonyl-fluoride-trifluoro, methane-(pentafluorothio)trifluoro, methane-bromo-difluoro-nitroso, methane-bromo-fluoro, methane-bromo-chloro-fluoro, methane-bromo-trifluoro, methane-chloro-difluoro-nitro, methane-chloro-dinitro, methane-chloro-fluoro, methane-chloro-trifluoro, methane-chloro-difluoro, methane-dibromo-difluoro, methane-dichloro-difluoro, methane-dichloro-fluoro, methane-difluoro, methane-difluoro-iodo, methane-disilano, methane-fluoro, methane-iodomethane-iodo-trifluoro, methane-nitro-trifluoro, methane-nitroso-trifluoro, methane-tetrafluoro, methane-trichloro-fluoro, methane-trifluoro, methanesulfenylchloride-trifluoro, 2-methyl butane, methyl ether, methyl isopropyl ether, methyl lactate, methyl nitrite, methyl sulfide, methyl vinyl ether, neopentane, nitrogen ($N_2$), nitrous oxide, 1,2,3-nonadecane tricarboxylic acid-2-hydroxytrimethylester, 1-nonene-3-yne, oxygen ($O_2$), oxygen 17 ($^{17}O_2$), 1,4-pentadiene, n-pentane, dodecafluoropentane (perfluoropentane), tetradecafluorohexane (perfluorohexane), perfluoroisopentane, perfluoroneopentane, 2-pentanone-4-amino-4-methyl, 1-pentene, 2-pentene {cis}, 2-pentene {trans}, 1-pentene-3-bromo, 1-pentene-perfluoro, phthalic acid-tetrachloro, piperidine-2,3,6-trimethyl, propane, propane-1,1,1,2,2,3-hexafluoro, propane-1,2-epoxy, propane-2,2 difluoro, propane-2-amino, propane-2-chloro, propane-heptafluoro-1-nitro, propane-heptafluoro-1-nitroso, perfluoropropane, propene, propyl-1,1,1,2,3,3-hexafluoro-2,3 dichloro, propylene-1-chloro, propylene-chloro-{trans}, propylene-2-chloro, propylene-3-fluoro, propylene-perfluoro, propyne, propyne-3,3,3-trifluoro, styrene-3-fluoro, sulfur hexafluoride, sulfur (di)-decafluoro($S_2F_{10}$), toluene-2,4-diamino, trifluoroacetonitrile, trifluoromethyl peroxide, trifluoromethyl sulfide, tungsten hexafluoride, vinyl acetylene, vinyl ether, neon, helium, krypton, xenon (especially rubidium enriched hyperpolarized xenon gas), carbon dioxide, helium, and air. Fluorinated gases (that is, a gas containing one or more fluorine molecules, such as sulfur hexafluoride), fluorocarbon gases (that is, a fluorinated gas which is a fluorinated carbon or gas), and perfluorocarbon gases (that is, a fluorocarbon gas which is fully fluorinated, such as perfluoropropane and perfluorbutane) are preferred.

While virtually any gas may be theoretically employed in the gaseous phase of the present invention, a particular gas may be chosen to optimize the desired properties of the resultant contrast medium and to fit the particular diagnostic application. It has been found, for example, that certain gases make more stable gas-filled liposomes upon shaking, than other gases, and such gases are preferred. It has also been found that certain gases provide better imaging results on diagnostic imaging such as ultrasound or MRI.

As an example of increasing stability of the gas-filled liposomes, it has been found that carbon dioxide<oxygen<air<nitrogen<neon= helium<perfluorocarbon gases. For these, as well as other, reasons fluorinated gases, particularly perfluorocarbon gases, are preferred.

Also, although in some cases soluble gases will function adequately as the gaseous phase in the present invention, substantially insoluble gases tend to result in greater stability than gases with higher solubility, particularly upon creation of the contrast agent on agitation. Also, it will be easier to keep a gaseous phase with such insoluble gases substantially separate from the aqueous lipid phase prior to agitation, in accordance with the present invention. Thus, substantially insoluble gases, as earlier defined, are preferred.

The quality of ultrasound images and the duration of such images also correlates with the solubility of the gas in the aqueous milieu. The decrease in gas solubility, in general, offers a better resolved image of longer duration on ultrasound.

Additionally, it has been generally observed that the size of a gas-filled liposomes produced on agitation correlates with the solubility of the gas in the aqueous milieu, with the gases of greater solubility resulting in larger gas-filled liposomes. It is also believed that the size of the liposomes may be influenced by the interaction of the gas with the inner wall of the liposomes. Specifically, it is believed that the interaction at the interface affects the tension and, consequently, the outward force of the interior gas on the interior lipid wall of the liposome. A decrease in tension allows for smaller liposomes by decreasing the force exerted by the interior gas, thus allowing the force exerted on the exterior of the liposome by the aqueous milieu to contract the gas-filled liposome.

The solubility of gases in aqueous solvents may be estimated by the use of Henry's Law, since it is generally applicable to pressures up to about 1 atmosphere pressure and for gases that are slightly soluble (Daniels, F. and Alberty, R. A., Physical Chemistry, 3rd Edition, Wiley & Sons, Inc., New York, 1966). As an example, atmospheric air possesses a solubility of 18.68 ml in 1 kg of water at 25° C., nitrogen maintains a solubility of approximately 18.8 ml $kg^{-1}$ at 25° C. Sulfur hexafluoride, on the other hand, has a solubility of approximately 5.4 ml $kg^{-1}$ at 25° C.

In sum, the fluorinated gases, fluorocarbon gases, and perfluorcarbon gases are preferred for reasons of stability, insolubility, and resultant liposome size. Particularly preferred are the fluorinated gas sulfur hexafluoride, and the perfluorocarbon gases perfluoropropane, perfluorobutane, perfluorocyclobutane, perfluoromethane, perfluoroethane, and perfluoropentane, especially perfluoropropane and perfluorobutane.

It should be noted that perfluorocarbons having less than five carbon atoms are gases at room temperature. Perfluoropentane, for example, is a liquid until about 27° C. Above this temperature it will occupy the headspace of the container. It has been demonstrated that perfluoropentane also may be used to fill the headspace (that is, the space in the vial above the lipid suspension phase) even at room temperature, however. By selecting a defined value of liquid perfluoropentane calculated to fill the headspace and adding the liquid to the container at low temperature, e.g., −20° C., and then evacuating the container (effectively removing the headspace of air) and then sealing the container, perfluoropentane will undergo a transition from liquid phase to vapor phase at a temperature lower than its boiling point at 1 atmosphere. Thus, at room temperature it will occupy some or all of the headspace with gas. As those skilled in the art will recognize, one may estimate the decrease in the liquid phase to vapor phase transition temperature by using a common "rule of thumb" estimate. Specifically, for every decrease in pressure by half, the boiling temperature will decrease by about 10° C. Alternatively, one may calculate the decrease in temperature as a function of decreased pressure by using relationships based upon the ideal gas law based upon Boyle's law. Another method for filling the headspace with perfluoropentane is to first evacuate the headspace and then to fill the headspace with perfluoropentane gas above 27° C. Of course, this method is not limited to perflubropentane alone, but applies to all perfluorocarbon gases, as well as gases in general, provided the boiling point of the gas is known.

If desired, two or more different gases may be used together to fill the headspace. A mixture of gases may have a number of advantages in a wide variety of applications of the resultant gas-filled liposomes (such as applications in ultrasound imaging, MR imaging, etc.). It has been found that a small amount of a substantially insoluble gas may be mixed with a soluble gas to provide greater stability than would be expected by the combination. For example, a small amount of perfluorocarbon gas (generally at least about 1 mole %, for example) may be mixed with air, nitrogen, oxygen, carbon dioxide or other more soluble gases. The resulting gas-filled liposome contrast agent produced post-agitation may then be more stable than the air, nitrogen, oxygen, carbon dioxide or other more soluble gases alone.

Additionally, the use of a mixture of gases may be used to compensate for the increase in gas-filled liposome size which might otherwise occur in vivo were pure perfluorocarbon gas containing liposomes to be injected in vivo. It has been found that some perfluorocarbon gases may tend to absorb or imbibe other gases such as oxygen. Thus, if the perfluorocarbon gas is injected intravenously, it may take up the oxygen or other soluble gases dissolved in the circulating blood. The resulting bubbles may then grow in vivo as a result of this uptake. Armed with a knowledge of this phenomenon, one may then premix the perfluorocarbon gas with a soluble gas, such as air, nitrogen, oxygen, carbon dioxide, thereby saturating the perfluorocarbon of its absorptive or imbibing properties. Consequently, this would retard or even eliminate the potential for expansion of the gas-filled liposomes in the bloodstream. This is significant in light of the fact that should a liposome grow to a size greater than 10 $\mu M$, potentially dangerous embolic events may occur if administered in the bloodstream. By filling the headspace with more soluble gases than perfluorocarbon gas, along with the perfluorocarbon gas, the gas-filled liposomes will generally not undergo this increase in size after injection in vivo. Thus, as a result of the present invention, the problem of embolic events as a result of liposome expansion may be circumvented by producing liposomes where such expansion is eliminated or sufficiently retarded.

Thus, in accordance with the present invention, if desired, a substantially insoluble gas may be combined with a soluble gas to efficiently produce highly effective and stable gas-filled liposomes.

Table 2 below provides an analysis of samples of gas-filled liposomes prepared using varying percentages of the substantially insoluble gas perfluoropropane (PFP) and air as headspace gases. The gases were combined with a lipid aqueous phase by agitating for 60 seconds at 3300 RPM. An Optical Particle Sizer (Particle Sizing Systems, Santa Barbara, Calif.) was used to analyze gas-filled liposome size and total counts. A sample volume of 5 microliters was used for each analysis, with four samples used for each determination.

As shown in Table 2, even when only 20% of the gas was PFP (a substantially insoluble gas) and 80% of the gas was air (a mixture of soluble gases), 100 fold more liposomes were produced than when air alone (0% PFP) was used. Moreover, when air alone (0% PFP) was used, the liposomes were much less stable and a larger fraction were above 10 microns. The 20% PFP and 80% air liposomes, however, appeared just as stable as the 80% PFP and 20% air liposomes, as well as the other intermediate PFP concentration samples, and the 20% PFP with 80% air produced about as many gas-filled liposomes as 80% PFP with 20% air.

allows one to use only a small amount of the substantially insoluble gas (e.g., a perfluorocarbon or other fluorinated gas) and primarily a more biocompatible (less potentially toxic) gas such as air or nitrogen to comprise most of the liposome volume.

The amount of substantially insoluble gases and soluble gases in any mixture may vary widely, as one skilled in the art will recognize. Typically, however, at least about 0.01% of the total amount of the gas is a substantially insoluble gas,

TABLE 2

Effect of Percent Perfluoropropane on Bubble Size and Number

| Gas % PFP | Number Weighted Mean | Volume Weighted Mean | Estimated Number of Particles | Percentage of Particles <10 µm | Estimated # of Particles per mL | Percentage of Particles >10 µm |
|---|---|---|---|---|---|---|
| 80% | | | | | | |
| Average | 2.37 | 28.76 | 5.45E+05 | 98.94 | 1.10E+09 | 1.05 |
| STDev | 0.07 | 0.82 | 4.67E+04 | 0.08 | 8.20E+07 | 0.07 |
| CV | 3% | 3% | 9% | 0% | 7% | 7% |
| 60% | | | | | | |
| Average | 2.14 | 20.75 | 5.87E+05 | 99.36 | 1.15E+09 | 0.64 |
| STDev | 0.02 | 5.93 | 7.08E+04 | 0.10 | 1.27E+08 | 0.09 |
| CV | 1% | 29% | 12% | 0% | 11% | 14% |
| 50% | | | | | | |
| Average | 2.13 | 30.35 | 5.23E+05 | 99.29 | 1.07E+09 | 0.68 |
| STDev | 0.07 | 12.15 | 1.49E+04 | 0.11 | 4.37E+07 | 0.10 |
| CV | 3% | 40% | 3% | 0% | 4% | 15% |
| 20% | | | | | | |
| Average | 2.00 | 13.64 | 5.35E+05 | 99.61 | 1.07E+09 | 0.41 |
| STDev | 0.04 | 6.79 | 2.26E+04 | 0.06 | 3.92E+07 | 0.07 |
| CV | 2% | 50% | 4% | 0% | 4% | 16% |
| 0% | | | | | | |
| Average | 2.30 | 93.28 | 5.03E+03 | 98.23 | 1.00E+07 | 1.93 |
| STDev | 0.21 | 66.05 | 4.96E+02 | 0.26 | 8.60E+05 | 0.36 |
| CV | 9% | 71% | 10% | 0% | 9% | 19% |

In Table 2, STDev=Standard Deviation, and CV=Coefficient of Variance. Also in Table 2, E+ denotes an exponent to a certain power, for example, 5.45E+05=5.45× $10^5$.

In short, it has been found that only a small amount of a relatively insoluble gas (such as PFP) is needed to stabilize the liposomes, with the vast majority of the gas being a soluble gas. Although the effective solubility of the combination of two or more gases, as calculated by the formula below $$\frac{(\text{solubility gas } A) \times (\text{mole percent gas } A) + (\text{solubility gas } B) \times (\text{mole percent gas } B)}{100}$$

may be only slightly different than the solubility of the soluble gas, there is still a high gas-filled liposome count and gas-filled liposome stability with only a small amount of insoluble gas in added.

Although not intending to be bound by any theory of operation, it is believed that the substantially insoluble gas is important for a membrane stabilizing effect. Indeed, it is believed that the substantially insoluble gas (such as PFP) acts as a barrier against the lipid membrane, possibly effectively forming a layer on the inner surface of the membrane, which retards egress of the soluble gas (such as air, nitrogen, etc.). This discovery is both surprising and useful, as this more preferably at least about 0.1%, even more preferably at least about 1%, and most preferably at least about 10%. Suitable ranges of substantially insoluble gas vary, depending upon various factors such as the soluble gas to be additionally employed, the type of lipid, the particular application, etc. Exemplary ranges include between about 0.01% to about 99% substantially insoluble gas, preferably between about 1% and about 95%, more preferably between about 10% and about 90%, and most preferably between about 30% and about 85%.

For other uses beyond diagnostic ultrasound imaging, such as uses in diagnostic magnetic resonance imaging (MRI), paramagnetic gases such as the strongly paramagnetic oxygen 17 gas ($^{17}O_2$), neon, xenon (especially rubidium enriched hyperpolarized xenon gas), or oxygen (which is still, albeit less strongly, paramagnetic), for example, are preferably used to fill the headspace, although other gases may be also used. Most preferably, $^{17}O_2$ gas, neon, rubidium enriched hyperpolarized xenon gas, or oxygen gas is combined with a substantially insoluble gas such as, for example, a perfluorocarbon gas. Paramagnetic gases are well known in the art and suitable paramagnetic gases will be readily apparent to those skilled in the art. The most preferred gas for MRI applications, whether used alone or in combination with another gas, is $^{17}O_2$.

By using a combination of gases, the $^{17}O_2$ or other paramagnetic gas provides the optimal contrast and the perfluorocarbon stabilizes the $^{17}O_2$ gas within the entrapped gas after agitation. Without the addition of the perfluorocarbon gas, gases such as $^{17}O_2$ is generally much less effective, since because of its solubility it diffuses out of the lipid entrapment after intravenous injection. Additionally $^{17}O_2$ gas is quite expensive. Combining the perfluorocarbon gas with $^{17}O_2$ gas greatly increases the efficacy of the product and decreases the cost through more efficient use of the costly $^{17}O_2$ gas. Similarly, other gases with desirable paramagnetic properties, such as neon, may be mixed with the perfluorocarbon gases.

As Table 3, below, reveals, a wide variety of different gases may be used in MR imaging application. In Table 3, the R2 ($1/T2/mmol/L.sec^{-1}$) for different gases in gas-filled liposomes are shown. As Table 3 shows, there are dramatic differences in the relaxivity of the different gas-filled liposomes, the higher the R2 relaxation values indicating the more effective the liposomes are as MR imaging agents. Of the gases shown, air has the highest R2 value. It is believed that air is the highest because of the paramagnetic effect of the oxygen in air. Pure oxygen, however, is somewhat less effective, likely due to the higher solubility of the oxygen and equilibration of oxygen into the aqueous milieu surrounding the liposomes. With air, the nitrogen (air is about 80% nitrogen) helps to stabilize the oxygen within the liposomes. Nitrogen has much less water solubility than air. As noted above, PFP or other perfluorocarbon gases may be mixed with a more magnetically active gas such as air, oxygen, $^{17}O_2$ or rubidium enriched hyperpolarized xenon. In so doing, stable highly magnetically active gas-filled liposomes may be prepared.

TABLE 3

Size Distribution and Relaxivity

| Gas | Number Weighted Distribution ($\mu$m) | Volume Weighted Distribution ($\mu$m) | $R_2$ |
| --- | --- | --- | --- |
| Nitrogen | 6.96 ± 0.63 | 31.08 ± 7.42 | 474.6 ± 59.9 |
| Sulfur Hexafluoride | 4.31 ± 0.13 | 44.25 ± 1.23 | 319.3 ± 42.5 |
| Xenon (Rb) | 7.02 ± 1.19 | 160.90 ± 92.46 | 191.2 ± 30.8 |
| Argon | 8.14 ± 0.49 | 41.45 ± 13.02 | 55.29 ± 41.3 |
| Air | 6.05 ± 1.05 | 23.28 ± 0.41 | 1510.4 ± 0.41 |
| Perfluoropropane | 4.24 ± 0.72 | 49.88 ± 11.11 | 785 ± 31.8 |
| Oxygen | 7.26 ± 0.98 | 30.99 ± 3.90 | 732.4 ± 73.9 |
| Neon | 7.92 ± 0.71 | 26.20 ± 1.03 | 595.1 ± 97.2 |
| Perfluorobutane | 5.88 ± 0.36 | 51.25 ± 3.97 | 580.1 ± 45.5 |

The headspace of the container may be filled with the gas at ambient, decreased or increased pressure, as desired.

In the container of the invention, the gaseous phase is substantially separate from the aqueous lipid suspension phase. By substantially separate, it is meant that less than about 50% of the gas is combined with the aqueous lipid phase, prior to agitation. Preferably, less than about 40%, more preferably less than about 30%, even more preferably less than about 20%, and most preferably less than about 10% of the gas is combined with the aqueous lipid phase. The gaseous phase is kept substantially separate from the aqueous lipid phase, until about the time of use, at which time the container is agitated and the gaseous phase and aqueous lipid phase combined to form an aqueous suspension of gas-filled liposomes. In this fashion, an excellent contrast agent for ultrasonic or magnetic resonance imaging is produced. Moreover, since the contrast agent is prepared immediately prior to use, shelf-life stability problems are minimized.

Figure 2:
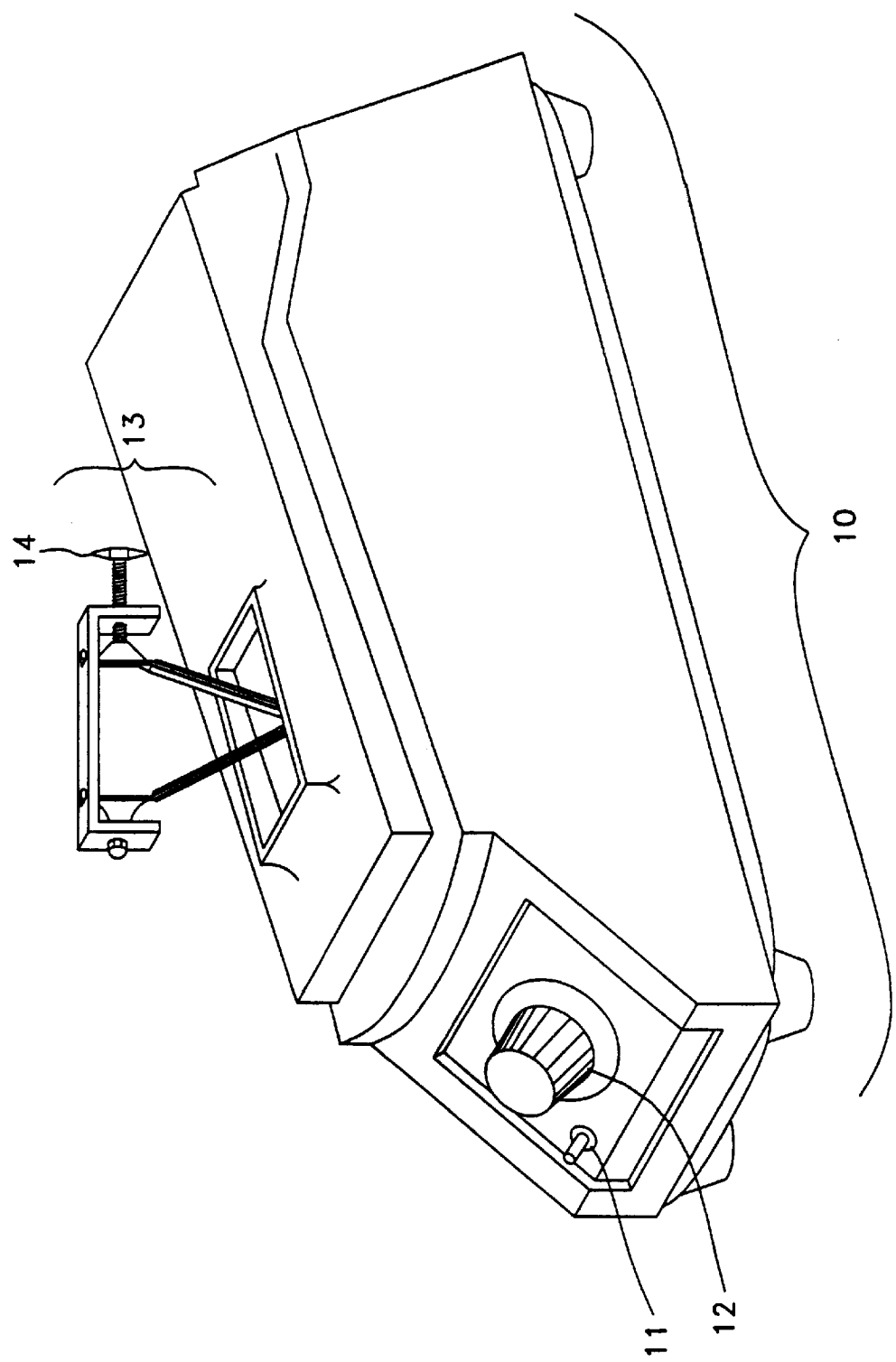
FIG. 2 is a diagram of an agitation device which may be employed to agitate the container of FIG. 1, thereby mixing the aqueous lipid suspension and the gas and producing a contrast agent for ultrasonic or magnetic resonance imaging.
Figure 3:
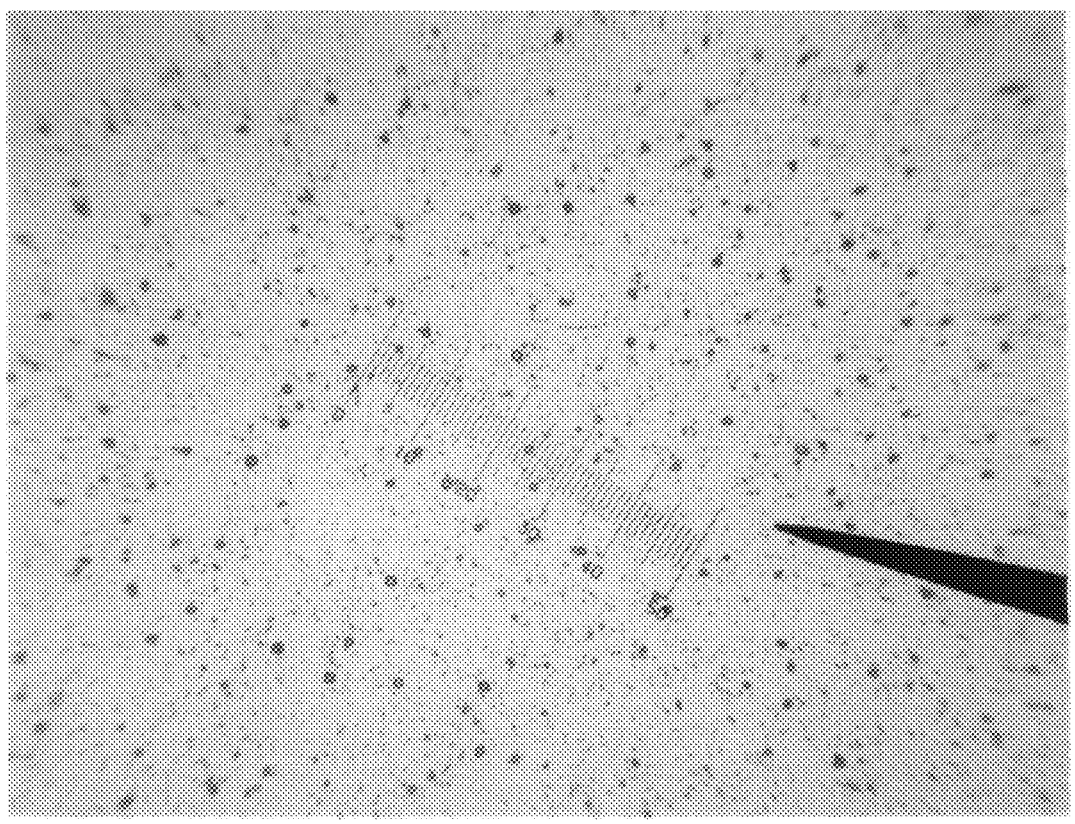
FIG. 3 is a photomicrograph of gas-filled liposomes produced using the container shown in FIG. 1 and the agitation device shown in FIG. 2.

Agitation may be carried out in a wide variety of ways and may include mechanical and/or hand agitation, as well as agitation by other means such as sonication (sound waves). Mechanical and/or hand agitation is preferred. Agitation may be carried out, for example, by shaking, stirring, vortexing, vibrating, etc. Preferably, an agitation device such as that depicted in FIG. 2 may be employed. Specifically, in FIG. 2, a mechanical agitation device (10) is shown. Agitation may be commenced and ceased using the start-stop button (11). Agitation device (10) also comprises a knob (12) which provides for variable speed (RPM) adjustment. By turning knob (12) in a clockwise fashion, increasing agitation speed (in RPMS) is achieved. Conversely, turning knob (12) in a counter-clockwise fashion decreases the agitation speed. The contents a container of the invention may be agitated by placing the container in the housing modulus (13) of agitation device (10). The housing modulus (13) serves as the agitation means of agitation device (10). To secure the container firmly in place in the housing modulus for agitation, a screw (14) is used.

The container employed in the present invention may take a variety of different forms. It may, if desired, be as shown in FIG. 1, the container (1) having a body (2) and cap (3), containing a headspace of gas (4) and an aqueous suspension of lipids (5) substantially separate from one another. Alternatively, the container may take the form of a pre-filled syringe, which may, if desired, be fitted with one or more filters. In this case, the syringes are filled with an aqueous phase and a headspace of a pre-selected gas. The syringes are generally mounted to the shaking device with their long axes oriented perpendicular to the direction of shaking. After shaking, the gas-filled liposomes are produced in the syringe, ready to use. Preferably, the container, whether it be a container of the type shown in FIG. 1, a syringe, or another type of container, along with its contents, is sterile.

A variety of different materials may be used to produce the containers of the invention, including the syringes, such as glass, borosilicate glass, silicate glass, polyethylene, polypropylene, polytetrafluoroethylene, polyacrylates, polystyrene, or other plastics. The preferred containers, including syringes, are either gas impermeable or wrapped within an outer gas impermeable barrier prior to filling with gas. This is, or course, desirable to maintain the integrity of the pre-selected gas within the container. Examples of syringe materials having gas-tight capabilities may include but are by no means limited to glass silicates or borosilicates, fitted with silica-fused syringes or luer-lock type syringes, and teflon-tipped or teflon-coated plungers.

As one skilled in the art would recognize, once armed with the substance of the present disclosure, various additives may be employed in the aqueous lipid suspension phase of the invention to stabilize that phase, or to stabilize the gas-filled liposomes upon agitation. If desired, these additives may be added to the aqueous lipid phase prior to agitation, or may be added to the composition after agitation and resultant preparation of the gas-filled liposomes. The use of such additives will, of course, be dependent upon the particular application intended for the resultant gas-filled liposomes, as will be readily apparent to those skilled in the art.

A number of stabilizing agents which may be employed in the present invention are available, including xanthan gum, acacia, agar, agarose, alginic acid, alginate, sodium alginate, carrageenan, dextran, dextrin, gelatin, guar gum, tragacanth, locust bean, bassorin, karaya, gum arabic, pectin, casein, bentonite, unpurified bentonite, purified bentonite, bentonite magma, colloidal, cellulose, cellulose (microcrystalline), methylcellulose, hydroxyethylcellulose, hydroxypropylcellulose, hydroxypropylmethylcellulose, carboxymethylcellulose, calcium carboxymethylcellulose, sodium carboxymethylcellulose, carboxymethylcellulose sodium 12, as well as other natural or modified natural celluloses, polysorbate, carbomer 934P, magnesium aluminum silicate, aluminum monostearate, polyethylene oxide, polyvinylalcohol, povidone, polyethylene glycol, propylene glycol, polyvinylpyrrolidone, silicon dioxide, silicon dioxide colloidal.

Also, compounds such as such as perfluorooctylbromide (PFOB), perfluorooctyliodide, perfluorotripropylamine, and perfluorotributylamine may be utilized in the lipid phase as stabilizing agents. Perfluorocarbons with greater than five carbon atoms will generally be liquid at body temperature, and such perfluorocarbons are also highly preferred as stabilizing agents. Suitable perfluorcarbons include perfluorohexane, perfluoroheptane, perfluorooctane, perfluorodecalin, and perfluorododecalin. In addition, perfluorinated lipids or partially fluorinated lipids may be used as well to help in stabilization. As will be apparent to those skilled in the art, a wide variety of perfluorinated and partially fluorinated analogs of the lipids described in the present invention may be used. Because of their relative hydrophobic nature with respect to the hydrocarbon lipids, such perfluorinated or partially fluorinated lipids may even provide advantages in terms of stability. Examples of perfluorinated or partially fluorinated lipids are $F_6C_{11}$ phosphatidylcholine(PC) and $F_8C_5PC$. Such analogs are described, for example, in Santaella et al., *Federation of European Biochemical Societies (FEBS)*, Vol. 336, No. 3, pp. 418–484 (1993), the disclosures of which are hereby incorporated herein by reference in their entirety.

A wide variety of biocompatible oils may also be used for the purpose of assisting stabilization, such as peanut oil, canola oil, olive oil, safflower oil, corn oil, almond oil, cottonseed oil, persic oil, sesame oil, soybean oil, mineral oil, mineral oil light, ethyl oleate, myristyl alcohol, isopropyl myristate, isopropyl palmitate, octyldodecanol, propylene glycol, glycerol, squalene, or any other oil commonly known to be ingestible. These may also include lecithin, sphingomyelin, cholesterol, cholesterol sulfate, and triglycerides.

Stabilization may also be effected by the addition of a wide variety of viscosity modifiers (i.e., viscosity modifying agents), which may serve as stabilizing agents in accordance with the present invention. This class of compounds include but are by no means restricted to; 1) carbohydrates and their phosphorylated and sulfonated derivatives; 2) polyethers with molecular weight ranges between 400 and 8000; 3) di- and trihydroxy alkanes and their polymers in the molecular weight range between 800 and 8000. Liposomes may also be used in conjunction with emulsifying and/or solubilizing agents which may consist of, but are by no means limited to, acacia, cholesterol, diethanolamine, glyceryl monostearate, lanolin alcohols, lecithin, mono- and diglycerides, monoethanolamine, oleic acid, oleyl alcohol, poloxamer, polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax, Pluronic F61, Pluronic F64 and Pluronic F68.

Other agents which may be added include tonicity agents such as polyalcohols such as glycerol, propylene glycol, polyvinylalcohol, polyethyeneglycol, glucose, mannitol, sorbitol, sodium chloride and the like.

If desired, anti-bactericidal agents and/or preservatives may be included in the formulation. Such agents include sodium benzoate, all quaternary ammonium salts, sodium azide, methyl paraben, propyl paraben, sorbic acid, potassium sorbate, sodium sorbate, ascorbylpalmitate, butylated hydroxyanisole, butylated hydroxytoluene, chlorobutanol, dehydroacetic acid, ethylenediamine tetraacetic acid (EDTA), monothioglycerol, potassium benzoate, potassium metabisulfite, potassium sorbate, sodium bisulfite, sulfur dioxide, and organic mercurial salts.

If desired, an osmolarity agent may be utilized to control the osmolarity. Suitable osmotically active materials include such physiologically compatible compounds as monosaccharide sugars, disaccharide sugars, sugar alcohols, amino acids, and various synthetic compounds. Suitable monosaccharide sugars or sugar alcohols include, for example, erythrose, threose, ribose, arabinose, xylose, lyxose, allose, altrose, glucose, mannose, idose, galactose, talose, trehalose, ribulose, fructose, sorbitol, mannitol, and sedoheptulose, with preferable monosaccharides being fructose, mannose, xylose, arabinose, mannitol and sorbitol. Suitable disaccharide sugars include, for example, lactose, sucrose, maltose, and cellobiose. Suitable amino acids include, for example, glycine, serine, threonine, cysteine, tyrosine, asparagine, glutamine, aspartic acid, glutamic acid, lysine, arginine and histidine. Synthetic compounds include, for example, glycerol, propylene glycol, polypropylene glycol, ethylene glycol, polyethylene glycol and polyvinyl-pyrrolidone. Various other suitable osmotically active materials are well known to those skilled in the art, and are intended to be within the scope of the term osmotically active agent as used herein.

A variety of polymers, such as those discussed above, may also be added for a variety of different purposes and uses.

As those skilled in the art would recognize, a wide range of additive amounts, such as the suspending agents described above, may be employed in the aqueous lipid suspension phase of the invention, as needed or desired, depending upon the particular end use. Such additives generally may comprise from between 0.01% by volume to about 95% by volume of the resultant contrast agent formulation, although higher or lower amounts may be employed. By way of general guidance, a suspending agent is typically present in an amount of at least about 0.5% by volume, more preferably at least about 1% by volume, even more preferably at least about 10% by volume. Generally the suspending agent is typically present in an amount less than about 50% by volume, more preferably less than about 40% by volume, even more preferably less than about 30% by volume. A typical amount of suspending agent might be about 20% by volume, for example. Also, typically, to achieve generally preferred ranges of osmolarity, less than about 25 g/l, more preferably less than about 20 g/l, even more preferably less than about 15 g/l, and still more preferably less than about 10 g/l of the osmotically active materials are employed, and in some instances no osmotically active materials are employed. A most preferred range of osmotically active materials is generally between about 0.002 g/l and about 10 g/l. These, as well as other, suitable ranges of additives will be readily apparent to those skilled in the art, once placed in possession of the present invention.

A wide variety of therapeutic and/or diagnostic agents may also be incorporated into the aqueous lipid suspension phase simply by adding the desired therapeutic or diagnostic agents to that phase. Suitable therapeutic and diagnostic agents, and suitable amounts thereof, will be readily apparent to those skilled in the art, once armed with the present disclosure. These agents may be incorporated into or onto the lipid membranes, or encapsulated in the resultant liposomes.

To further improve the magnetic effect of the resultant gas-filled liposomes for MRI, for example, one or more MRI contrast enhancing agents, such as paramagnetic or superparamagnetic contrast enhancing agents, may be added. Useful MRI contrast enhancing agents include paramagnetic ions such as transition metals, including iron ($Fe^{+3}$), copper ($CU^{+2}$), and manganese ($Mn^{+2}$) and the lanthanides such as gadolinium ($Gd^{+3}$) and dysprosium ($Dy^{+3}$), nitroxides, iron oxides ($Fe_3O_4$), iron sulfides and paramagnetic particles such as manganese ($Mn^{+2}$) substituted hydroxyapatites. As well, agents such as chromium ($Cr^{+3}$), nickel ($Ni^{+2}$), cobalt ($Co^{+2}$) and europium ($Eu^{+2}$) are other examples of paramagnetic ions that may be used. Other contrast enhancing agents such as nitroxide radicals or any other atom that maintains an unpaired electron spin with paramagnetic properties may be used. Ideally, the contrast enhancing agent is added to the aqueous lipid phase prior to agitation, and is designed such that after agitation, the contrast enhancing agent is incorporated into or onto the surface of the resultant gas-filled liposome, although addition after liposome preparation is also possible. The resulting gas-filled liposome may have greatly enhanced relaxivity, providing an especially effective contrast agent for magnetic resonance imaging. By way of example, manganese ($Mn^{+2}$) will incorporate itself onto the head groups of the lipid when phosphatidylcholine or phosphatidylserine is used in the aqueous lipid phase. If desired, the metals may be chelated using liposoluble compounds as shown, for example, in Unger et al., U.S. Pat. No. 5,312,617, the disclosures of which are hereby incorporated herein by reference, in their entirety. Such liposoluble compounds are quite useful, as they will readily incorporate into the liposome membrane. Iron oxides and other particles should generally be small, preferably less than about $1\mu$, more preferably less than about 200 nm, and most preferably less than 100 nm, to achieve optimal incorporation into or onto the liposome surface. For improved incorporation, iron oxides coated with aliphatic or lypophyllic compounds may be used as these will tend to incorporate themselves into the lipid coating of the bubble surface.

It also is within the realm of the present invention that the aqueous lipid suspension phase may contain an ingredient to cause gelation with lipid polymers and metals which do not spontaneously gel, or to enhance gelation, gelling agents such as polyvalent metal cations, sugars and polyalcohols may be employed. Exemplary polyvaleht metal cations useful as gelling agents include calcium, zinc, manganese, iron and magnesium. Useful sugars include monosaccharides such as glucose, galactose, fructose, arabinose, allose and altrose, disaccharides such as maltose, sucrose, cellobiose and lactose, and polysaccharides such as starch. Preferably, the sugar is a simple sugar, that is, monosaccharide or a disaccharide. Polyalcohol gelling agents useful in the present invention include, for example, glycidol, inositol, mannitol, sorbitol, pentaerythritol, galacitol and polyvinylalcohol. Most preferably, the gelling agent employed in the present invention is sucrose and/or calcium. The particular gelling agents which may be employed in the various formulations of the present invention will be readily apparent to one skilled in the art, once armed with the present disclosure. Combinations of lipids, e.g. phosphatidic acid with calcium or magnesium salts and polymers such as alginic acid, hyaluronic acid or carboxymethyl cellulose may be used to stabilize lipids. It is hypothesized that the divalent cations form metal bridges between the lipids and polymers to stabilize the gas-filled liposomes within the lipid/polymeric systems. Similarly, suspensions containing mixtures of chitosan (or chitin-based materials), polylysine, polyethyleneimine and alginic acid (or its derivatives) or hyaluronic acid may be prepared.

It has been found that the rate of agitation, the amount of the lipids comprising the aqueous lipid phase, and the size of the sealed container may affect the ultimate size of any gas-filled liposome. In addition, it has been found that the proportions of such agents may be important as well to the size distribution of the gas-filled liposomes. It is also believed that the surface tension at the gas-filled liposome interface and the aqueous milieu is an additional determining factor in the ultimate size of the gas-filled liposome, when taken into account along with the rate of shaking, the vial size, and the lipid concentration.

In a sterile container filled with an aqueous phase and a headspace of gas it has been discovered how changes may be easily and simply made so as to change liposome size post-agitation and thereby obtain a product with liposomes of the desired size distribution. Additionally, filters may be used to further refine the size distribution of the contrast agent after shaking. The following provides a review of how changes in the components of the invention may be used to modify liposome size.

First, it has been discovered that the different materials within the aqueous phase may be important in controlling resultant gas-filled liposome size. Table 4 shows the sizes of liposomes produced by shaking sterile containers filled with an aqueous phase and a headspace of nitrogen. In all cases, the liposome size was measured by a Particle Sizing System Model 770 light obscuration particle sizer (Particle Sizing Systems, Santa Barbara, Calif.) As the data reveals, the ratio of lipids in the aqueous phase affects the size distribution of the resulting gas-filled liposomes. Specifically, Table 4 below shows the effect of lipid composition on the average liposome size.

TABLE 4

Effect of Lipid composition on Average Liposome Size

| Lipid Composition* | Average Liposome Size |
|---|---|
| 77.5:15:7.5 | 5.26 µm |
| 77.5:20:2.5 | 7.33 µm |
| 82:10:8 | 6.02 µm |

*Ratios of dipalmitoylphosphatidylcholine:dipalmitoylphosphatidic acid:dipalmitoylphosphatidylethanolamine-PEG5000, in mole %.

Table 5 demonstrates the dependence of the concentration of a defined lipid composition mixture upon the average liposome size. As shown in Table 5, variations in the total concentrations of lipid are also important in affecting liposome size after shaking. In these experiments the ratio of the three different lipid components was held constant and the concentration of lipid was varied between 0.5 and 5.0 mg $ml^{-1}$ in the aqueous phase. The gas used was nitrogen. The optimal size bubbles for ultrasonic diagnosis with a headspace of perfluorobutane was produced when the lipid concentration in the aqueous phase was 1.0 mg $ml^{-1}$.

TABLE 5

Effect of Lipid Concentration on Average Liposome Size

| Lipid Concentration* | Average Liposome Size |
| --- | --- |
| 1 mg ml$^{-1}$ | 1.8 μm |
| 3 mg ml$^{-1}$ | 4.0 μm |
| 5 mg ml$^{-1}$ | 7.2 μm |

*Lipid concentration for all samples was based upon a mole % ratio of dipalmitoylphosphatidylcholine:dipalmitoylphosphatidic acid:dipalmitoylphosphatidylethanolamine-PEG5000 of 82:10:8. The gas used was nitrogen.

The size of liposomes may also depend on the composition of the gas in the headspace in addition to the concentration of stabilizing media, e.g. lipids. For example it has been discovered that a 1.0 mg ml$^{-1}$ lipid concentration produces gas-filled liposomes of about the same diameter when nitrogen is used, as the 5.0 mg ml$^{-1}$ concentration of lipids with perfluorobutane. However, it has been found that the higher concentration may result in a distribution skewed a bit more towards larger gas-filled liposomes. This phenomenon tends to reflect the increased stability of the gas-filled liposomes at higher lipid concentration. It is therefore believed that the higher concentration of lipid either contributes to the stability by acting as a stabilizing agent in the aqueous phase or, the higher lipid concentration provides more lamellae around the gas, making them more stable, and thus allowing a greater proportion of the larger liposomes to persist. Additionally it has been discovered that the size of the headspace of gas may also be used to affect gas-filled liposome size. Larger headspaces containing proportionately more gas relative to the size of the aqueous phase will generally produce larger liposomes than smaller sized headspaces.

The speed of agitation is important to generate the proper sized liposomes. It has been found that agitation speeds between 100 and 10,000 revolutions per minute (RPMs) can be used to make liposomes, however, there are optimums in terms of rapidly and reproducibly producing liposomes of defined size. One revolution, as that term is used herein, refers to a single back and forth, up and down, side to side, circular, etc., motion, where the motion begins and ends at (that is, returns to) the point of origin. Table 3 shows the sizes of liposomes produced from an aqueous phase of 82 mole % dipalmitoylphosphatidylcholine (DPPC), with 10 mole % dipalmitoyl-phosphatidic acid (DPPA) with 8 mole % dipalmitoylphosphatidyl-ethanolamine-PEG5000 (DPPE-PEG5000), and a headspace comprising perfluorpropane gas. The preparations were shaken for two minutes on a Wig-L-Bug™ (Crescent Dental Mfg., Lyons, Ill.). Utilizing 2 ml amber vials (Wheaton Industries, Millville, N.J.; acutal volume 3.7 ml) filled with an aqueous lipid phase and a headspace of gas, the multi-phase container of the present invention was placed on the Wig-L-Bug™ and the speed was measured via a Co-Palmer Model 08210 Pistol Grip tachometer (Code-Palmer, Nile, Ill.). Table 6 provides the results, and demonstrates the effect of agitation rates on the resultant average liposome size.

TABLE 6

Effect of Agitation Rate on Average Liposome Size

| Speed (RPM) | Average Liposome Size |
| --- | --- |
| 1500 | 3.4 μm |
| 2800 | 3.3 μm |
| 3300 | 2.9 μm |

Indeed, it has been discovered that there is an optimal agitation speed for producing the liposomes of desired size. At the optimum speed, the gas-filled liposomes form very quickly, in less than 5 minutes, even within a minute or two, and even within 30 seconds or less. It is noted that the method and motion of shaking is significant in the formation of proper sized liposomes. In particular, it has been found that optimal sized liposomes occur when the reciprocal motion of the shaking occurs in the form of an arc. It is preferred that the degree of the arc motion be between 2° and 20°. It is even more preferred that the degree of the arc motion be between 4° and 10°. It is yet more preferred that the degree of the arc motion be between 5° and 8°. It is most preferred that the degree of the arc motion be between 6° and 7°. As a further embodiment of this invention, it has been discovered that the number of RPMs is preferably between about 500 and about 10,000, more preferably between about 1000 and about 5000, and most preferably between about 2500 and about 4000.

It is also an important discovery of this invention that the size, shape, and amount of headspace available for the liquid contents to agitate is also vital to the formation of optimally sized gas-filled liposomes. For example, it is a discovery of this invention that when using vials of 3.7 ml actual volume (Wheaton 300 Borosilicate glass, Wheaton Industries, Millville, N.J., referred to as 2 ml size, diameter×height=15 mm×32 mm), the volume of the gas-containing headspace is preferably between about 10% and about 60% of the total volume of the vial. Generally, the gas-containing headspace in a vial is between about 10% and about 80% of the total volume of that vial, although depending upon the particular circumstances and desired application, more or less gas may be appropriate. More preferably, the headspace comprises between about 30% and about 70% of the total volume. It generally most preferred that the volume of gas-containing headspace comprise about 60% of the total volume of the vial.

Hence, it is clear from the above discussion of the invention that the optimal size is dependent upon a variety of factors, including the intensity and motion of agitation, and the size, shape, and actual filling volume of the vials.

Although a variety of different agitation devices may be used to prepare the gas-filled liposomes, such as paint mixers, table top shakers and vortexers, the geometry of shaking and speed are important for optimizing the production of the gas-filled liposomes. The Wig-L-Bug™ is the most preferred device for agitation.

The size of the sterile container, the geometry of the container and the orientation of the container with respect to the shaking apparatus all are important in the determination of the gas-filled liposome size. The shaking device, e.g., Wig-L-Bug™, will generally shake more slowly as the weight of the sterile container increases beyond a certain level. The standard Wig-L-Bug™ shakes more quickly with a 2 ml vial (actual volume 3.7 ml) than a 10 ml vial. This experiment was performed utilizing a 10 ml clear vial (Wheaton Industries, Millville, N.J.) and a 2 ml (actual volume 3.7 ml) amber vial (Wheaton Industries, Millville, N.J.). Once again, using a Code-Palmer Pistol Grip tachometer (Code-Palmer, Nile, Ill.), the rate of shaking was measured. Table 7 lists the results.

Table 7 demonstrates the dependence of the shaking rate of an electrical shaker on the size of the vial used for shaking.

TABLE 7

Effect of Vial Size on Wig-L-Bug ™ Shaking Rate

| Vial Size | Measured Rate (RPM) |
|---|---|
| 2 ml vial | 3250 |
| 10 ml vial | 2950 |

In general, the invention is practiced with sterile containers wherein the aqueous phase is already present within the bottle. For selected applications however, the stabilizing media may be stored within the container in a dried or lyophilized state. In this case the aqueous solution, e.g. sterile phosphate buffered saline, is added to the sterile container immediately prior to shaking. In so doing, the rehydrated stabilizing media within the aqueous phase will again interact with the gas headspace during shaking so as to produce gas-filled liposomes as above. Rehydration of a dried or lyophilized suspending medium necessarily further complicates the product and is generally undesired but for certain preparations may be useful for further extending the shelf life of the product. For example, certain therapeutic agents such as cyclophosphamide, peptides, and genetic materials (such as DNA), might be hydrolyzed on long term aqueous storage. Rehydration of a previously lyophilized sample to form the aqueous phase and headspace prior to shaking can make it practical to produce gas-filled liposomes containing compounds which otherwise might not have sufficient shelf life.

The foregoing sets forth various parameters in determining gas-filled liposome size. Liposome size is of importance in terms of maximizing product efficacy and minimizing toxicity. Additionally the liposomes should be as flexible as possible both to maximize efficacy and to minimize adverse tissue interactions such as lodging in the lungs. The present invention creates liposomes of the desired size with very thin compliant membranes. Because the liposome membranes are so thin and compliant, e.g. only 1 mg ml$^{-1}$ of lipid is necessary for stabilizing the membranes, it has been found that gas-filled liposomes of larger diameter may be used without producing pulmonary hypertension. For example, pigs have been administered doses up five time the necessary diagnostic imaging dose without any evidence of pulmonary hypertension. By comparison much lower doses of smaller diameter albumin coated air bubbles in these animals cause severe pulmonary hypertension. Because the liposomes of the present invention are so flexible and deformable, they easily slide through the lung capillaries. Additionally the coating technologies employed with the present lipids (e.g. polyethyleneglycol bearing lipids) decreases adverse pulmonary interactions while at the same time enhancing the in vitro and in vivo stability and efficacy of the product.

The size of gas-filled liposomes for use as general ultrasound contrast media should be as large as possible (without causing embolic effects) because backscatter or the ultrasound effect is proportional to the radius to the sixth power when frequencies are such that the gas-filled liposomes are in the Rayleigh scattering regime. For MRI, larger liposomes of the invention are also preferred. The ability of the present invention to prepare and employ larger liposome size with less potential of toxic effects increases its efficacy relative to other products.

An additional parameter influencing ultrasound contrast is the elasticity of the liposome membrane. The greater the elasticity the greater the contrast effect. Because the present liposomes are coated by ultra-thin membranes of lipid elasticity is quite similar to naked gas and reflectivity and contrast effect are maximized.

The agitation procedure of the present invention readily produces liposomes from an aqueous phase and a headspace of gas within a sterile container. The invention is sufficient for producing liposomes with highly desirable properties for ultrasonic or magnetic resonance imaging applications. For selected applications however, a filter may be employed to produce liposbmes with even more homogeneous size distributions and of desired diameters. For example for measuring in vivo pressures on ultrasound using gas-filled liposome harmonic phenomena, it may be useful to have very tightly defined liposome diameters within a narrow range of sizes. This is readily accomplished by injecting the liposomes (produced by shaking the container with aqueous phase and headspace of gas) through a filter of defined size. The resulting liposomes will be no larger than a very close approximation of the size of the filter pores in the filter membrane. As noted above, for many ultrasonic or MRI applications, it is desirable to have the gas-filled liposomes be as large as possible. For certain applications however, much smaller gas-filled liposomes may be desirable. In targeting, for example, to tumors or other diseased tissues, it may be necessary for the gas-filled liposomes to leave the vascular space and to enter the tissue interstitium. Much smaller gas-filled liposomes may be useful for these applications. These smaller gas-filled liposomes (e.g., appreciably under a micron in diameter) can to a large extent be produced by modifications in the compounds in the aqueous phase (composition and concentration), as well as the headspace (composition of gas and volume of headspace), but also by injection through a filter. Very small gas-filled liposomes of substantially homogeneous size may be produced by injecting through for example a 0.22 micron filter. The resulting nanometer sized gas-filled liposomes may then have desirable properties for targeting.

The above examples of lipid suspensions may also be sterilized via autoclave without appreciable change in the size of the suspensions. Sterilization of the contrast medium may be accomplished by autoclave and/or sterile filtration performed either before or after the agitation step, or by other means known to those skilled in the art.

After filling the containers with the aqueous phase and the headspace of the pre-selected gas the sealed bottles may be stored indefinitely. There need be no particles to precipitate, gas-filled liposomes to burst or other untoward interactions between gas-filled liposomes, particles, colloids or emulsions. The shelf life of the container filled with the aqueous phase and headspace of gas depends only on the stability of the compounds within the aqueous phase. These properties of long shelf life and sterilizability confer substantial advantages to the present invention over the prior art. The problem of stability, such as with aggregation and precipitation of particles, which was so common in the field of ultrasound contrast media have been addressed herein.

The gas-filled liposomes which are produced by agitation of the multi-phase container of the invention have been found to have excellent utility as contrast agents for diagnostic imaging, such as ultrasound or magnetic resonance imaging. The liposomes are useful in imaging a patient generally, and/or in specifically diagnosing the presence of diseased tissue in a patient. The imaging process may be carried out by administering a gas-filled liposome of the invention to a patient, and then scanning the patient using ultrasound or magnetic resonance imaging to obtain visible images of an internal region of a patient and/or of any diseased tissue in that region. By region of a patient, it is meant the whole patient, or a particular area or portion of the patient. The liposomal contrast agent may be employed to provide images of the vasculature, heart, liver, and spleen, and in imaging the gastrointestinal region or other body cavities, or in other ways as will be readily apparent to those skilled in the art, such as in tissue characterization, blood pool imaging, etc. Any of the various types of ultrasound or magnetic resonance imaging devices can be employed in the practice of the invention, the particular type or model of the device not being critical to the method of the invention.

The gas-filled liposomes of the invention may also be employed to deliver a wide variety of therapeutics to a patient for the treatment of various diseases, maladies or afflictions, as one skilled in the art will recognize.

Also, magnetically active liposomes may be used for estimating pressure by MRI. The liposomes increase the bulk susceptibility and, accordingly, increase $T_2$ relaxation but even more so for $T_2^*$ relaxation. Because the effects of static field gradients are mainly compensated in spin echo experiments (by virtue of the 180° radiofrequency refocusing pulse) the effect of the liposomes is less marked on $T_2$ than $T_2^*$ weighted pulse sequences where static field effects are not compensated. Increasing pressure results in loss of liposomes or liposome disruption (for more soluble gases) as well as a decrease in liposome diameter. Accordingly, $1/T_2$ decreases with increasing pressure. After release of pressure some of the remaining liposomes re-expand and $1/T_2$ increases again slightly. Liposomes composed of about 80% PFP with 20% air show enhanced stability and a slight fall in $1/T_2$ with pressure which returns to baseline after release of pressure (i.e., the liposomes are stable but show a slight $1/T_2$ pressure effect). When gradient echo images are obtained and signal intensity measured these effects are much more marked. Signal intensity increases with increasing pressure ($1/T_2^*$ decreases with increased pressure). Because the experiment is performed relatively quickly (it takes less than a tenth the time to perform the gradient echo images than to measure $T_2$). The duration of exposure to pressure is much less and the nitrogen filled liposomes return nearly to baseline after pressure release (i.e. there is very little loss of liposomes). Accordingly, the signal intensity on gradient echo falls back nearly to baseline at return to ambient pressure. For measurement of pressure by MRI, the liposomes may be designed either to fall apart with increasing pressure or to be stable but decrease liposome diameter with increasing pressure. Because on MRI liposome radius affects $1/T_2^*$, this relationship can be used to estimate pressure by MRI.

As one skilled in the art would recognize, administration of the gas-filled liposomes to the patient may be carried out in various fashions, such as intravenously or intraarterially by injection, orally, or rectally. The useful dosage to be administered and the particular mode of administration will vary depending upon the age, weight and the particular mammal and region thereof to be scanned or treated, and the particular contrast medium or therapeutic to be employed. Typically, dosage is initiated at lower levels and increased until the desired contrast enhancement or therapeutic effect is achieved. The patient can be any type of mammal, but most preferably is a human.

The following actual examples are intended to illustrate how the present invention is employed, as well as some of the areas of extraordinary utility of the invention. These examples are exemplary only, and should not be construed as limiting the scope of the appended claims.

EXAMPLES

Example 1

Formation of Nitrogen Gas-Filled Liposomes

Gas-filled lipid bilayers were prepared in two 20 ml vials with 6 ml of a diluent containing normal (physiological) saline:propylene glycol:glycerol (8:1:1, v:v:v). To this was added in a final concentration of 5 mg ml$^{-1}$, a mixture of dipalmitoylphosphatidylcholine (DPPC):dipalmitoylphosphatidic acid (DPPA):dipalmitoylphosphatidyl-ethanolamine-PEG5000 (DPPE-PEG5000) in a molar ratio of 82:10:8 (mole %). The samples were then sealed with airtight and pressure maintaining septum caps. They were then purged and evacuated at least three times with nitrogen gas (99.98%, Arizona Welding Co., Tucson, Ariz.). The samples were then either autoclaved for 15 minutes at 121° C. in a Barnstead Model C57835 Steam Sterilizer (Barnstead/Thermolyne Corporation, Dubuque, Iowa) or sterile filtered from one to three times through a Nuclepore 0.22 gm filter (Costar, Pleasanton, Calif.). Samples were then removed from the autoclave and allowed to cool to approximately ambient temperatures. Samples were then vortexed on a Wig-L-Bug vortexer (Crescent Dental Mfg. Co., Lyons, Ill.) for a duration of two minutes. The resultant mixtures were then significant for the formation of gas-filled bilayers which resembled a foam. The gas-filled lipid bilayers were then sized by three methods on a Particle Sizing Systems Model 770 light obscuration detector (Particle Sizing Systems, Santa Barbara, Calif.), a Reichert-Jung Model 150 Optical Microscope equipped with a calibration eyepiece (Cambridge Instruments, Buffalo, N.Y.), and a Coulter Model (Coulter Industries, Luton Beds, England). Samples displayed an average number weighted size of about 5–7 microns with at least 95% of the particles smaller than 10 microns.

Example 2

Formation of Perfluoropentane Gas-Filled Liposomes

Gas-filled lipid bilayers were prepared in two 20 ml vials with 6 ml of a diluent containing normal (physiological) saline:propylene glycol:glycerol (8:1:1, v:v:v). To this was added in final concentrations varying between 1 mg ml$^{-1}$ and 5 mg ml$^{-1}$, a mixture of dipalmitoylphosphatidylcholine (DPPC):phosphatidic acid:dipalmitoylphosphatidylethanolamine-PEG 5000 in a weight ratio of 82:10:8 (w:w:w). To this mixture was added 50 µL (30.1 µmoles) perfluoropentane (PCR, Gainesville, Fla.). Samples were made at −20° C. and sealed with airtight and pressure maintaining septum caps. The samples were then autoclaved for 15 minutes at 121° C. in a Barnstead Model C57835 Steam Sterilizer (Barnstead/Thermolyne Corporation, Dubuque, Iowa). Samples were then removed from the autoclave and allowed to cool to approximately 40° C. Samples were then vortexed on a Wig-L-Bug™ vortexer (Crescent Dental Mfg. Co., Lyons, Ill.) for a duration of two minutes. The resultant mixtures were then significant for the formation of gas-filled bilayers which resembled a foam. The volume and height of the foam was recorded and one sample was placed into a −20° C. freezer (Kenmore Brand, Sears-Roebuck, Chicago, Ill.). The sample was then removed after 3 hours, at which time, it was noted that approximately 90% of the original volume remained. The sample was left in the freezer overnight (approximately 17 hours) and removed at which time it was discovered that 50% of the original volume remained. The remaining vial, used as a control, was maintained in a 30° C. incubator for the same time period. It was found that no loss in volume occurred, indicative that the cooling of the gas within the gas-filled bilayers had condensed, thereby decreasing the gas volume. Finally, the cold sample was then placed in the 30° C. incubator, where it was found that after approximately 45 minutes, 20% of the original foam volume had been restored. This is indicative of the fact that the condensed gas had once again volatilized and expanded the size of the gas-filled liposomes.

Example 3

Formulation of Perfluoropropane Gas-Filled Liposomes

The same procedure was utilized as in Example 1 except the gas utilized was perfluoropropane (99.99%, Alcon Surgical, Fort Worth, Tex.) and the vial size utilized was a 2 ml amber vial (actual volume=3.7 ml) (Wheaton, Millville, N.J.). The vials were filled with 1.5 ml of the lipid/diluent vehicle mixture. The process was sized via the same method as in Example 1, however, this time, producing a size of 4–6 microns with greater than 95% of the particles being less than 10 microns.

Example 4

Formulation of Perfluorobutane Gas-Filled Liposomes

The same procedure was utilized as in Example 1 except the gas utilized was perfluorobutane (97+%, Flura Corporation, Nashville, Tenn.) and the vial size utilized was a 2 ml amber vial (actual volume=3.7 ml) (Wheaton, Millville, N.J.). The vials were filled with 1.5 ml of the lipid/diluent vehicle mixture. The process was sized via the same method as in Example 1, however, this time, producing a size of 4–6 microns with greater than 95% of the particles being less than 10 microns.

Example 5

Formulation of Perfluorocyclobutane Gas-Filled Liposomes

The same procedure was utilized as in Example 1 except the gas utilized was perfluorocyclobutane (99.8%, Pfaltz & Bauer, Waterbury, Conn.) and the vial size utilized was a 2 ml amber vial (actual volume=3.7 ml) (Wheaton, Millville, N.J.). The vials were filled with 1.5 ml of the lipid/diluent vehicle mixture. The process was sized via the same method as in Example 1, however, this time, producing a size of 4–6 microns with greater than 95% of the particles being less than 10 microns.

Example 6

Formulation of Sulfur Hexafluoride Gas-Filled Liposomes

The same procedure was utilized as in Example 1 except the gas utilized was sulfur hexafluoride (99.99%, Alcon Surgical, Fort Worth, Tex.) and the vial size utilized was a 2 ml amber vial (actual volume=3.7 ml) (Wheaton, Millville, N.J.). The vials were filled with 1.5 ml of the lipid/diluent vehicle mixture. The process was sized via the same method as in Example 1, however, this time, producing a size of 4–6 microns with greater than 95% of the particles being less than 10 microns.

Example 7

Stability of Perfluorobutane Gas-Filled Liposomes Under Pressure Using In Vitro Acoustic Attenuation Testing Perfluorobutane gas-filled lipid bilayers formulated as described in Example 4. Samples varying in lipid concentrations between 1 mg ml$^{-1}$ and 5 mg ml$^{-1}$ were taken in 200 µL aliquots and diluted 10,000:1 in normal saline as the diluent. The samples were initially mixed with a magnetic stirrer to induce homogeneity and then turned off. A stainless steel plate was used as a perfect reflector, situated approximately 25 cm from the origin of the transducer. The transducer utilized was a 5.0 MHz broadband non-focused immersion transducer (Panametrics, Waltham Mass.). All data was transferred via a 488.2 GPIB board (National Instruments, Austin, Tex.) and processed on a Gateway 2000 80486 processor.

Prior to sampling of the gas-filled lipid bilayers, a baseline control was performed in normal saline only. Immediately after control conditions were established, the 200 µL aliquot was added to the saline solution and the data accumulated for 90 seconds at ambient temperature (20° C.). Attenuation (see FIG. 4) of the sound was constant over the 90 seconds with an attenuation of 2.0±0.5 dB cm$^{-1}$. A second sample was obtained whereby the pressure of the sample was then raised to 120 mm Hg and the attenuation recorded. As in the ambient temperature experiment, the attenuation remained constant with little variation over the 90 second testing period however the attenuation was approximately between 0.9 dB cm$^{-1}$. Another sample was then measured under conditions of constant temperature of 37° C. Once again, over the 90 second period, the attenuation was constant and the attenuation approximated 0.9 db cm$^{-1}$. A final sample was measured at 37° C. and a pressure of 120 mm Hg. This time the attenuation decreased in a linear fashion with time from 0.9 dB cm$^{-1}$ to 0.4 dB cm$^{-1}$ over 90 seconds. This demonstrated the increased stability of this formulation over the nitrogen-filled lipid bilayers.

Example 8

Stability of Nitrogen Gas-Filled Liposomes Under Pressure Using In Vitro Acoustic Attenuation Testing The identical experiments as in Example 7 were performed except the gas-filled lipid bilayers were composed of nitrogen gas as described in Example 1. The attenuation was significant for stable attenuation at both ambient temperature (20° C.) and human body temperature (37° C.), however, upon exposing the contents of the dilution to 120 mm Hg pressure, the attenuation precipitously dropped close to baseline control values. This demonstrated the lack of stability with nitrogen-filled lipid bilayers under pressure compared to perfluorobutane-filled lipid bilayers.

Example 9

Effect of Lipid Concentration on Number Weighted Average Size of Perfluorocyclobutane Gas-Filled Liposomes Perfluorocyclobutane gas-filled lipid bilayers were prepared as described in Example 5 except at 3 different concentrations of lipid formulation. The formulation was comprised of a diluent containing normal (physiological) saline:propylene glycol:glycerol (8:1:1, v:v:v). To this was added in final concentrations varying between 1 mg ml$^{-1}$ and 5 mg ml$^{-1}$ a mixture of dipalmitoylphosphatidylcholine (DPPC):dipalmitoylphosphatidic acid (DPPA):dipalmitoylphosphatidylethanolamine-PEG5000 (DPPE-PEG5000) in a molar ratio of 82:10:8 (mole %). Samples were prepared in 2 ml vials (actual volume=3.7 ml) (Wheaton Industries, Millville, N.J.) and sized on a Particle Sizing Systems Model 770 light obscuration sizing system. The following table describes the results.

Table 9 demonstrates the effect of lipid concentration on the average size of perfluorocarbon gas-filled lipid bilayers using perfluorocyclobutane as the example.

TABLE 9

Effect of Lipid Concentration on Perfluorocyclobutane Gas-filled Liposomes

| Lipid Concentration | Number Weighted Average Size |
|---|---|
| 1.0 mg ml$^{-1}$ | 3.1 µm |
| 3.0 mg ml$^{-1}$ | 3.8 µm |
| 5.0 mg ml$^{-1}$ | 4.7 µm |

Example 10

Demonstration of Lack of Hemodynamic Changes Utilizing Substantially Insoluble Gas-Filled Liposomes Samples of gas-filled lipid bilayers containing the lipid mixtures as described in Examples 3, 4, 5, and 6 were prepared with total lipid concentrations of 1 mg ml$^{-1}$ and 3 mg ml$^{-1}$ lipid using perfluoropropane (PFP), pefluorocyclobutane (PFCB), perflurobutane (PFB) and sulfur hexafluoride (SHF). Imaging was performed in a mongrel dog weighing approximately 28 kg. using a Model 52005 Acoustic Imaging ultrasound machine equipped with a 5 megahertz transducer. The animal was sedated with sodium pentobarbital, ventilated on room air and monitored for pulmonary arterial pressure, systemic arterial pressure and pulse rate. Imaging of the heart was performed in the short axis position and the animal received bolus doses of 5 microliters per kg of PFP, PFCB, PFB and SHF testing both the 1 mg ml$^{-1}$ and 3 mg ml$^{-1}$ lipid concentrations. At least 15 minutes was allowed between each injection to allow for clearance of any residual contrast. All of the perfluorocarbon filled liposomes (PFP, PFCB and PFB) showed myocardial perfusion enhancement at 1 mg ml$^{-1}$ lipid but PFB more intensely than the others. PFP improved at 3 mg ml$^{-1}$. The SHF filled liposomes did not show demonstrable myocardial perfusion enhancement at 1 mg per ml lipid but did show pronounced myocardial enhancement at 3 mg per ml lipid.

The above was substantially repeated in another dog and the same results obtained.

Hemodynamic studies were performed in another dog using perfluoropropane filled liposomes. The animal received multiple doses via rapid bolus of up to 300 microliters per kilogram each, i.e. 50 times higher than the imaging dose. The animal showed absolutely no change in any hemodynamic parameters despite multiple doses demonstrating the high hemodynamic safety of the agent.

Example 11

Determination of Therapeutic Ratio (Window) Based Upon Toxicity Testing in Balb/C Mice Toxicity testing was performed in Balb/C mice weighing between about 20 and 25 grams. The LD$_5$'s of 1 mg ml$^{-1}$ lipid concentrations of liposomes entrapping samples of perfluoropropane (PFP), perfluorocyclobutane (PFCB), perfluorobutane (PFB), and sulfur hexafluoride (SHF) were tested via rapid bolus. The LD$_{50}$'s of each of the PFCB, PFB and PFP samples were each greater than 12 ml kg$^{-1}$ and for the SHF gas-filled lipid bilayers, greater than 30 mg kg$^{-1}$, indicating therapeutic indexes of greater than 2,400 to 1 and 6,000 to 1 respectively for these products useful in ultrasonic diagnosis.

Example 12

Use of Perfluoropentane Gas-Filled Liposomes as an Ultrasound Contrast Agent

New Zealand White Rabbits were anesthetized with an intramuscular injection of 1 cc kg$^{-1}$ Rabbit Mix (8:5:2:, v:v:v, xylazine, 20 mg ml$^{-1}$:ketamine, 10 mg ml$^{-1}$:acepromazine, 100 mg ml$^{-1}$). Rabbits were imaged on an Acoustic Imaging Model 5200 diagnostic ultrasound and an Acoustic Imaging Model 5200S diagnostic Color Doppler instrument (Acoustic Imaging, Phoenix, Ariz.). Rabbits were injected via a 23 G butterfly catheter through the marginal ear vein. The rabbit was given doses ranging from 0.01 cc kg$^{-1}$ to 0.1 cc kg$^{-1}$ of the perfluoropentane-filled lipid bilayers over the span of 5–10 seconds. Long-axis views utilizing a 7.5 MHz transducer revealed brilliant imaging of all four chambers of the heart and myocardium for a period ranging from 20 minutes to over one hour. The transducer was then moved over the liver region, where brilliant contrast was observed in the hepatic vein, hepatic portal vein, as well as the hepatic sinuses. The transducer was then placed over the kidney which revealed contrast in the medulla and cortex regions as well as visualization of the renal artery. The diagnostic ultrasound transducer was then replaced with a color doppler, and sustained and brilliant contrast throughout all vascularized tissues of the animal's body was observed.

Example 13

Effect of Different Concentrations of Perfluoropropane and Air on Number and Size of Gas-Filled Liposomes Multiple samples of lipid solutions (1 mg per mL; 82:10:8 mole % ratios of DPPC:DPPA:DPPE-PEG-5000) in 8:1:1 weight ratios of normal saline:glycerol:proplyene glycol in 2 ml vials (actual size 3.7 ml) Wheaton Industries (Millville, N.J.) were placed on a modified Edwards Model SO4 lyophilizer with four cubic foot capacity and subjected to reduced pressure. The headspaces of the vials were then instilled with 80% PFP with 20% air, 60% PFP with 40% air, 50% PFP with 50% air, 20% PFP with 80% air, or 100% air. The percentages of gas in the headspaces of the different samples were confirmed by gas chromatography a Hewlett Packard Gas Chromatograph Model 1050L interfaced with Hewlett Packard Chem™ softward. The mode of detection was Flame ionization detection. The samples were then shaken at 3,300 RPM for 60 seconds using the Wig-L-Bug™ and the sizes and liposomes counts determined by optical particle sizing as previously described. The results are shown above in Table 2.

The disclosures of each of the patents and publications cited or referred to herein are hereby incorporated herein by reference in their entirety.

Various modifications of the invention in addition to those shown and described herein will be apparent to those skilled in the art from the foregoing description. Such modifications are also intended to fall within the scope of the appended claims.

What is claimed is:

1. A container comprising an aqueous lipid suspension phase and a gaseous phase, wherein said gaseous phase is substantially separate from said aqueous lipid suspension phase and consists essentially of a single perfluorocarbon gas, and said aqueous lipid suspension phase comprises at least one phosphatidylcholine, at least one phosphatidylethanolamine, and at least one phosphatidic acid, wherein said phosphatidylcholine is selected from the group consisting of dioleoylphosphatidylcholine, dimyristoylphosphatidylcholine, dipalmitoylphosphatidylcholine, and distearoylphosphatidylcholine; said phosphatidylethanolamine is selected from the group consisting of dipalmitoylphosphatidylethanolamine, dioleoylphosphatidylethanolamine, and N-succinyl-dioleoylphosphatidylethanolamine; and said phosphatidic acid is dipalmatoylphosphatidic acid.

2. A container of claim 1 wherein said perfluorocarbon gas is selected from the group consisting of perfluoromethane, perfluoroethane, perfluoropropane, perfluorobutane, perfluorocyclobutane, perfluoropentane, and perfluorohexane.

3. A container of claim 2 wherein said perfluorocarbon gas is perfluoropropane.

4. A container of claim 2 wherein said perfluorocarbon gas is perfluoropentane.

5. A container of claim 2 wherein said perfluorocarbon gas is perfluorohexane.

6. A container of claim 1 wherein said aqueous lipid suspension phase further comprises a targeting ligand.

7. A container of claim 6 wherein said targeting ligand is polyethyleneglycol or polyvinylpyrrolidone.

8. A container of claim 1 wherein said phosphatidylethanolamine is present in an amount of from about 2.5 mole percent to about 8.0 mole percent based on total moles of said lipids in said aqueous lipid suspension phase.

9. A container of claim 1 wherein said phosphatidylcholine, said phosphatidylethanolamine, and said phosphatidic acid are in a mole percent ratio of about 82%:8%:10%.

10. A container of claim 1 wherein said phosphatidylcholine is dipalmitoylphosphatidylcholine, said phosphatidylethanolamine is dipalmitoylphosphatidylethanolamine, and said phosphatidic acid is dipalmitoylphosophatidic acid.

11. A container of claim 10 wherein said phosphatidylethanolamine is dipalmitoylphosphatidylethanolamine-PEG5000.

12. A container of claim 11 wherein said dipalmitoylphosphatidylethanolamine-PEG5000 is present in an amount from about 2.5 mole percent to about 8 mole percent based on total moles of said lipids in said aqueous lipid suspension phase.

13. A container of claim 12 wherein said dipalmitoylphosphatidylcholine, said dipalmitoylphosphatidylethanolamine-PEG5000, and said dipalmitoylphosophatidic acid are in a mole percent ratio of about 82%:8%:10%.

14. A container of claim 1 wherein at least a portion of said lipids are in a lipid monolayer in said aqueous lipid suspension phase.

15. A container of claim 14 wherein said aqueous lipid suspension phase further comprises polyethyleneglycol.

16. A container of claim 14 wherein said perfluorocarbon gas is perfluoropropane.

17. A container of claim 14 wherein said perfluorocarbon gas is perfluoropentane.

18. A container of claim 14 wherein said perfluorocarbon gas is perfluorohexane.

19. A container of claim 1 wherein at least a portion of said lipids are in a lipid bilayer in said aqueous lipid suspension phase.

20. A container of claim 19 wherein said aqueous lipid suspension phase further comprises polyethyleneglycol.

21. A container of claim 19 wherein sad perfluorocarbon gas is perfluoropropane.

22. A container of claim 19 wherein said perfluorocarbon gas is perfluoropentane.

23. A container of claim 19 wherein said perfluorocarbon gas is perfluorohexane.

24. A container of claim 1 wherein at least a portion of said lipids are in a lipid multilayer in said aqueous lipid suspension phase.

25. A container of claim 24 wherein said aqueous lipid suspension phase further comprises polyethyleneglycol.

26. A container of claim 24 wherein said perfluorocarbon gas is perfluoropropane.

27. A container of claim 24 wherein said perfluorocarbon gas is perfluoropentane.

28. A container of claim 24 wherein said perfluorocarbon gas is perfluorohexane.

29. A container of claim 1 wherein said aqueous lipid suspension phase has been rehydrated from a lyophilized composition.

30. A container of claim 1 wherein said aqueous lipid suspension phase further comprises a therapeutic or diagnostic agent.

31. A container of claim 30 wherein said diagnostic agent is an MRI contrast enhancing agent.

32. A container of claim 31 wherein said MRI contrast enhancing agent is a paramagnetic ion.

33. A container of claim 1 wherein said aqueous lipid suspension phase further comprises a suspending agent.

34. A container of claim 1 wherein said aqueous lipid suspension phase further comprises a viscosity modifying agent.

35. A container of claim 1 wherein said container is sterilized.

36. A container which contains a composition for use in diagnostic imaging, wherein the composition comprises an aqueous lipid suspension phase and a gaseous phase, wherein said gaseous phase is substantially separate from said aqueous lipid suspension phase and consists essentially of a single perfluorocarbon gas, and said aqueous lipid suspension phase comprises at least one phosphatidylcholine, at least one phosphatidylethanolamine, and at least one phosphatidic acid, wherein said phosphatidylcholine is selected from the group consisting of dioleoylphosphatidylcholine, dimyristoylphosphatidylcholine, dipalmitoylphosphatidylcholine, and distearoylphosphatidylcholine; said phosphatidylethanolamine is selected from the group consisting of dipalmitoylphosphatidylethanolamine, dioleoylphosphatidylethanolamine, and N-succinyl-dioleoylphosphatidylethanolamine; and said phosphatidic acid is dipalmatoylphosphatidic acid.

37. A container of claim 36 wherein said diagnostic imaging is ultrasound imaging or magnetic resonance imaging.

38. A container comprising an aqueous lipid suspension phase and a gaseous phase, wherein said gaseous phase comprises a fluorinated gas and is substantially separate from said aqueous lipid suspension phase, and said aqueous lipid suspension phase comprises at least one phosphatidylcholine, at least one phosphatidylethanolamine, and at least one phosphatidic acid, wherein said phosphatidylcholine is selected from the group consisting of dioleoylphosphatidylcholine, dimyristoylphosphatidylcholine, dipalmitoylphosphatidylcholine, and distearoyl-phosphatidylcholine; said phosphatidylethanolamine is selected from the group consisting of dipalmitoylphosphatidylethanolamine, dioleoyl-phosphatidylethanolamine, and N-succinyl-dioleoyl-phosphatidylethanolamine; and said phosphatidic acid is dipalmatoylphosphatidic acid.

39. A container of claim 38 wherein said fluorinated gas is sulfur hexafluoride or a perfluorocarbon.

40. A container of claim 39 wherein said fluorinated gas is sulfur hexafluoride.

41. A container of claim 39 wherein said fluorinated gas is a perfluorocarbon.

42. A container of claim 31 wherein said perfluorocarbon is selected from the group consisting of perfluoromethane, perfluoroethane, perfluoropropane, perfluorobutane, perfluorocyclobutane, perfluoropentane, and perfluorohexane.

43. A container of claim 42 wherein said perfluorocarbon is perfluoropropane.

44. A container of claim 43 wherein said gaseous phase further comprises nitrogen.

45. A container of claim 42 wherein said perfluorocarbon is perfluoropentane.

46. A container of claim 45 wherein said gaseous phase further comprises nitrogen.

47. A container of claim 42 wherein said perfluorocarbon is perfluorohexane.

48. A container of claim 47 wherein said gaseous phase further comprises nitrogen.

49. A container of claim 38 wherein said gaseous phase further comprises air, oxygen, nitrogen, carbon dioxide, or combinations thereof.

50. A container of claim 38 wherein said gaseous phase further comprises a paramagnetic gas.

51. A container of claim 50 wherein said paramagnetic gas is selected from the group consisting of oxygen, oxygen$^{17}$ ($^{17}O_2$), neon, Xenon, and rubidium enriched hyperpolarized xenon.

52. A container of claim 38 wherein said gaseous phase comprises said fluorinated gas selected from the group consisting of perfluoropropane, perfluorobutane, perfluorocyclobutane, perfluoromethane, perfluoroethane, perfluoropentane, perfluorohexane, sulfur hexafluoride, and a second gas selected from the group consisting of air, nitrogen, oxygen, carbon dioxide, neon, helium, krypton, xenon, rubidium enriched hyperpolarized xenon, and oxygen$^{17}$ ($^{17}O_2$).

53. A container of claim 38 wherein said aqueous lipid suspension phase further comprises a targeting ligand.

54. A container of claim 53 wherein said targeting ligand is polyethyleneglycol or polyvinylpyrrolidone.

55. A container of claim 38 wherein said phosphatidylethanolamine is present in an amount of from about 2.5 mole percent to about 8.0 mole percent based on total moles of said lipids in said aqueous lipid suspension phase.

56. A container of claim 38 wherein said phosphatidylcholine, said phosphatidylethanolamine, and said phosphatidic acid are in a mole percent ratio of about 82%:8%:10%.

57. A container of claim 38 wherein said phosphatidylcholine is dipalmitoylphosphatidylcholine, said phosphatidylethanolamine is dipalmitoylphosphatidylethanolamine, and said phosphatidic acid is dipalmitoylphosophatidic acid.

58. A container of claim 57 wherein said phosphatidylethanolamine is dipalmitoylphosphatidylethanolamine-PEG5000.

59. A container of claim 58 wherein said dipalmitoylphosphatidylethanolamine-PEG5000 is present in an amount from about 2.5 mole percent to about 8 mole percent based on total moles of said lipids in said aqueous lipid suspension phase.

60. A container of claim 59 wherein said dipalmitoylphosphatidylcholine, said dipalmitoylphosphatidylethanolamine-PEG5000, and said dipalmitoylphosophatidic acid are in a mole percent ratio of about 82%:8%:10%.

61. A container of claim 38 wherein at least a portion of said lipids are in a lipid monolayer in said aqueous lipid suspension phase.

62. A container of claim 61 wherein said aqueous lipid suspension phase further comprises polyethyleneglycol.

63. A container of claim 61 wherein said fluorinated gas is sulfur hexafluoride.

64. A container of claim 61 wherein said fluorinated gas is perfluoropropane.

65. A container of claim 64 wherein said gaseous phase further comprises nitrogen.

66. A container of claim 61 wherein said fluorinated gas is perfluoropentane.

67. A container of claim 66 wherein said gaseous phase further comprises nitrogen.

68. A container of claim 61 wherein said fluorinated gas is perfluorohexane.

69. A container of claim 68 wherein said gaseous phase further comprises nitrogen.

70. A container of claim 38 wherein at least a portion of said lipids are in a lipid bilayer in said aqueous lipid suspension phase.

71. A container of claim 70 wherein said aqueous lipid suspension phase further comprises polyethyleneglycol.

72. A container of claim 70 wherein said fluorinated gas is sulfur hexafluoride.

73. A container of claim 70 wherein said fluorinated gas is perfluoropropane.

74. A container of claim 73 wherein said gaseous phase further comprises nitrogen.

75. A container of claim 70 wherein said fluorinated gas is perfluoropentane.

76. A container of claim 75 wherein said gaseous phase further comprises nitrogen.

77. A container of claim 70 wherein said fluorinated gas is perfluorohexane.

78. A container of claim 77 wherein said gaseous phase further comprises nitrogen.

79. A container of claim 38 wherein at least a portion of said lipids are in a lipid multilayer in said aqueous lipid suspension phase.

80. A container of claim 79 wherein said aqueous lipid suspension phase further comprises polyethyleneglycol.

81. A container of claim 79 wherein said fluorinated gas is sulfur hexafluoride.

82. A container of claim 79 wherein said fluorinated gas is perfluoropropane.

83. A container of claim 82 wherein said gaseous phase further comprises nitrogen.

84. A container of claim 79 wherein said fluorinated gas is perfluoropentane.

85. A container of claim 84 wherein said gaseous phase further comprises nitrogen.

86. A container of claim 79 wherein said fluorinated gas is perfluorohexane.

87. A container of claim 86 wherein said gaseous phase further comprises nitrogen.

88. A container of claim 38 wherein said aqueous lipid suspension phase has been rehydrated from a lyophilized composition.

89. A container of claim 38 wherein said aqueous lipid suspension phase further comprises a therapeutic or diagnostic agent.

90. A container of claim 89 wherein said diagnostic agent is an MRI contrast enhancing agent.

91. A container of claim 90 wherein said MRI contrast enhancing agent is a paramagnetic ion.

92. A container of claim 38 wherein said aqueous lipid suspension phase further comprises a suspending agent.

93. A container of claim 38 wherein said aqueous lipid suspension phase further comprises a viscosity modifying agent.

94. A container of claim 38 wherein said container is sterilized.

95. A container which contains a composition for use in diagnostic imaging, wherein the composition comprises an aqueous lipid suspension phase and a gaseous phase, wherein said gaseous phase comprises a fluorinated gas and is substantially separate from said aqueous lipid suspension phase, and said aqueous lipid suspension phase comprises at least one phosphatidylcholine, at least one phosphatidylethanolamine, and at least one phosphatidic acid, wherein said phosphatidylcholine is selected from the group consisting of dioleoylphosphatidylcholine, dimyristoylphosphatidylcholine, dipalmitoylphosphatidylcholine, and distearoylphosphatidylcholine; said phosphatidylethanolamine is selected from the group consisting of dipalmitoylphosphatidylethanolamine, dioleoylphosphatidylethanolamine, and N-succinyl-dioleoyl-phosphatidylethanolamine; and said phosphatidic acid is dipalmatoylphosphatidic acid.

96. A container of claim 95 wherein said diagnostic imaging is ultrasound imaging or magnetic resonance imaging.

97. A container comprising an aqueous lipid suspension phase and a gaseous phase, wherein said gaseous phase is substantially separate from said aqueous lipid suspension phase and comprises a substantially insoluble gas in combination with a soluble gas, and said aqueous lipid suspension phase comprises lipids, wherein said lipids comprise at least one phosphatidylcholine, at least one phosphatidylethanolamine, and at least one phosphatidic acid wherein said phosphatidylcholine is selected from the group consisting of dioleoylphosphatidylcholine, dimyristoylphosphatidylcholine, dipalmitoylphosphatidylcholine, and distearoylphosphatidylcholine; said phosphatidylethanolamine is selected from the group consisting of dipalmitoylphosphatidylethanolamine, dioleoylphosphatidylethanolamine, and N-succinyl-dioleoyl-phosphatidylethanolamine; and said phosphatidic acid is dipalmatoylphosphatidic acid.

98. A container of claim 97 wherein said substantially insoluble gas is sulfur hexafluoride or a perfluorocarbon.

99. A container of claim 98 wherein said substantially insoluble gas is sulfur hexafluoride.

100. A container of claim 98 wherein said substantially insoluble gas is a perfluorocarbon.

101. A container of claim 100 wherein said perfluorocarbon is selected from the group consisting of perfluoromethane, perfluoroethane, perfluoropropane, perfluorobutane, perfluorocyclobutane, perfluoropentane, and perfluorohexane.

102. A container of claim 101 wherein said perfluorocarbon is perfluoropropane.

103. A container of claim 102 wherein said soluble gas is nitrogen.

104. A container of claim 101 wherein said perfluorocarbon is perfluoropentane.

105. A container of claim 104 wherein said soluble gas is nitrogen.

106. A container of claim 101 wherein said perfluorocarbon is perfluorohexane.

107. A container of claim 106 wherein said soluble gas is nitrogen.

108. A container of claim 97 wherein said soluble gas is air, oxygen, nitrogen, carbon dioxide, or combinations thereof.

109. A container of claim 97 wherein said substantially insoluble gas or soluble gas comprises a paramagnetic gas.

110. A container of claim 109 wherein said paramagnetic gas is selected from the group consisting of oxygen, oxygen$^{17}$ ($^{17}O_2$), neon, xenon, and rubidium enriched hyperpolarized xenon.

111. A container of claim 97 wherein said substantially insoluble gas is selected from the group consisting of perfluoropropane, perfluorobutane, perfluorocyclobutane, perfluoromethane, perfluoroethane, perfluoropentane, perfluorohexane, and sulfur hexafluoride, and said soluble gas is selected from the group consisting of air, nitrogen, oxygen, and carbon dioxide.

112. A container of claim 97 wherein said aqueous lipid suspension phase further comprises a targeting ligand.

113. A container of claim 112 wherein said targeting ligand is polyethyleneglycol or polyvinylpyrrolidone.

114. A container of claim 97 wherein said phosphatidylethanolamine is present in an amount of from about 2.5 mole percent to about 8.0 mole percent based on total moles of said lipids in said aqueous lipid suspension phase.

115. A container of claim 97 wherein said phosphatidylcholine, said phosphatidylethanolamine, and said phosphatidic acid are in a mole percent ratio of about 82%:8%:10%.

116. A container of claim 97 wherein said phosphatidylcholine is dipalmitoylphosphatidylcholine, said phosphatidylethanolamine is dipalmitoylphosphatidylethanolamine, and said phosphatidic acid is dipalmitoylphosophatidic acid.

117. A container of claim 116 wherein said phosphatidylethanolamine is dipalmitoylphosphatidylethanolamine-PEG5000.

118. A container of claim 117 wherein said dipalmitoylphosphatidylethanolamine-PEG5000 is present in an amount from about 2.5 mole percent to about 8 mole percent based on total moles of said lipids in said aqueous lipid suspension phase.

119. A container of claim 118 wherein said dipalmitoylphosphatidylcholine, said dipalmitoylphosphatidylethanolamine-PEG5000, and said dipalmitoylphosophatidic acid are in a mole percent ratio of about 82%:8%:10%.

120. A container of claim 97 wherein at least a portion of said lipids are in a lipid monolayer in said aqueous lipid suspension phase.

121. A container of claim 120 wherein said aqueous lipid suspension phase further comprises polyethyleneglycol.

122. A container of claim 120 wherein said substantially insoluble gas is sulfur hexafluoride.

123. A container of claim 120 wherein said substantially insoluble gas is perfluoropropane.

124. A container of claim 123 wherein said soluble gas is nitrogen.

125. A container of claim 120 wherein said substantially insoluble gas is perfluoropentane.

126. A container of claim 125 wherein said soluble gas is nitrogen.

127. A container of claim 120 wherein said substantially insoluble gas is perfluorohexane.

128. A container of claim 127 wherein said soluble gas is nitrogen.

129. A container of claim 97 wherein at least a portion of said lipids are in a lipid bilayer in said aqueous lipid suspension phase.

130. A container of claim 129 wherein said aqueous lipid suspension phase further comprises polyethyleneglycol.

131. A container of claim 129 wherein said substantially insoluble gas is sulfur hexafluoride.

132. A container of claim 129 wherein said substantially insoluble gas is perfluoropropane.

133. A container of claim 132 wherein said soluble gas is nitrogen.

134. A container of claim 129 wherein said substantially insoluble gas is perfluoropentane.

135. A container of claim 134 wherein said soluble gas is nitrogen.

136. A container of claim 129 wherein said fluorinated gas is perfluorohexane.

137. A container of claim 136 wherein said soluble gas is nitrogen.

138. A container of claim 97 wherein at least a portion of said lipids are in a lipid multilayer in said aqueous lipid suspension phase.

139. A container of claim 138 wherein said aqueous lipid suspension phase further comprises polyethyleneglycol.

140. A container of claim 138 wherein said substantially insoluble gas is sulfur hexafluoride.

141. A container of claim 138 wherein said substantially insoluble gas is perfluoropropane.

142. A container of claim 141 wherein said soluble gas is nitrogen.

143. A container of claim 138 wherein said substantially insoluble gas is perfluoropentane.

144. A container of claim 143 wherein said soluble gas is nitrogen.

145. A container of claim 138 wherein said substantially insoluble gas is perfluorohexane.

146. A container of claim 145 wherein said soluble gas is nitrogen.

147. A container of claim 97 wherein said aqueous lipid suspension phase has been rehydrated from a lyophilized composition.

148. A container of claim 97 wherein said aqueous lipid suspension phase further comprises a therapeutic or diagnostic agent.

149. A container of claim 148 wherein said diagnostic agent is an MRI contrast enhancing agent.

150. A container of claim 149 wherein said MRI contrast enhancing agent is a paramagnetic ion.

151. A container of claim 97 wherein said aqueous lipid suspension phase further comprises a suspending agent.

152. A container of claim 97 wherein said aqueous lipid suspension phase further comprises a viscosity modifying agent.

153. A container of claim 97 wherein said container is sterilized.

154. A container which contains a composition for use in diagnostic imaging, wherein the composition comprises an aqueous lipid suspension phase and a gaseous phase, wherein said gaseous phase is substantially separate from said aqueous lipid suspension phase and comprises a substantially insoluble gas in combination with a soluble gas, and said aqueous lipid suspension phase comprises at least one phosphatidylcholine, at least one phosphatidylethanolamine, and at least one phosphatidic acid, wherein said phosphatidylcholine is selected from the group consisting of dioleoylphosphatidylcholine, dimyristoylphosphatidylcholine, dipalmitoylphosphatidylcholine, and distearoyl-phosphatidylcholine; said phosphatidylethanolamine is selected from the group consisting of dipalmitoylphosphatidylethanolamine, dioleoyl-phosphatidylethanolamine, and N-succinyl-dioleoyl-phosphatidylethanolamine; and said phosphatidic acid is dipalmatoylphosphatidic acid.

155. A container of claim 154 wherein said diagnostic imaging is ultrasound imaging or magnetic resonance imaging.

* * * * *

UNITED STATES PATENT AND TRADEMARK OFFICE
CERTIFICATE OF CORRECTION

PATENT NO. : 6,551,576 B1
DATED : April 22, 2003
INVENTOR(S) : Unger et al.

It is certified that error appears in the above-identified patent and that said Letters Patent is hereby corrected as shown below:

Title page,
Item [60], Related U.S. Application Data, following "1996," please insert
-- now Pat. No. 6,146,657 --; following "1994," please insert -- now Pat. No. 5,773,024 --; following "07/569,828," please insert -- filed on Aug. 20, 1990, now Pat. No. 5,088,499 --; following "1993," please insert -- now Pat. No. 5,469,854 --; and following "1993", please insert -- now Pat. No. 5,580,575 --.
Item [56], References Cited, U.S. PATENT DOCUMENTS, "4,229,360 11/1991", reference, please delete "4,229,360 A" and insert -- 4,229,360 B1 -- therefor.
FOREIGN PATENT DOCUMENTS, "WO 84/02909", reference, please delete "8/1994" and insert -- 8/1984 -- therefor.
OTHER PUBLICATIONS, "Yang et al.," reference, please delete "Facture" and insert -- Fracture --
"Fukuda et al.," reference, please delete "Diotadecyldimethylammonium" and insert -- Dioctadecyldimethylammonium -- therefor.
"Regen," reference, please delete "Polymerizaed" and insert -- Polymerized -- therefor.
"Shiina et al.," reference, please delete "Hyperthermiably" and insert -- Hyperthermia by -- therefor.
"Ter-Pogossian," reference, please delete "*Tomography*, Kee, et al., n." after "*Computed Body*," please insert -- *Tomography*, Lee, et al., -- therefor.
"Aronberg," reference, please delete "Kee" and insert -- Lee -- therefor.
"Keller," reference, please delete "Microcirulation" and insert -- Microcirculation -- therefor.
"Villanueva et al.," reference, please delete "Patters" and insert -- Patterns -- therefor.

Column 1,
Line 7, following "Nov. 1, 1996," please insert -- now U.S. Pat. No. 6,146,657 --.
Line 8, following "Sep. 16, 1994," please insert -- now U.S. Pat. No. 5,773,024 --.
Line 39, following "08/076,239," please insert -- now U.S. Pat No. 5,469,854 --.
Line 40, following "08/076,250," please insert -- now U.S. Pat No. 5,580,575 --.

Column 3,
Line 48, please delete "dipalmatoylphosphatidic" and insert
-- dipalmitoylphosphatidic -- therefor.

Column 8,
Line 8, please delete "perflubropentane" and insert -- perfluoropentane -- therefor.

Column 13,
Line 9, please delete the second occurrence of "such as".

UNITED STATES PATENT AND TRADEMARK OFFICE
CERTIFICATE OF CORRECTION

PATENT NO. : 6,551,576 B1
DATED : April 22, 2003
INVENTOR(S) : Unger et al.

It is certified that error appears in the above-identified patent and that said Letters Patent is hereby corrected as shown below:

Column 15,
Line 49, please delete "polyvaleht" and insert -- polyvalent -- therefor.

Column 20,
Line 9, please delete "liposbmes" and insert -- liposomes -- therefor.

Column 22,
Line 14, please delete "0.22 gm" and insert -- 0.22 $\mu$m -- therefor.

Column 25,
Line 30, please delete "Model 52005" and insert -- Model 5200S -- therefor.
Line 62, please delete "Ld$_5$'s" and insert -- LD$_{50}$'s -- therefor.

Column 27,
Line 14, please delete "dipalmatoylphosphatidic" and insert
-- dipalmitoylphosphatidic -- therefor.

Column 29,
Line 8, please delete "dipalmatoylphosphatidic" and insert -- dipalmitoylphosphatidic -- therefor.

Column 31,
Line 35, please delete "dipalmatoylphospharidic" and insert
-- dipalmitoylphosphatidic -- therefor.
Line 56, please delete "dipalmatoylphosphatidic" and insert
-- dipalmitoylphosphatidic -- therefor.

Column 32,
Line 66, following "gas", please insert -- is --.

UNITED STATES PATENT AND TRADEMARK OFFICE
CERTIFICATE OF CORRECTION

PATENT NO. : 6,551,576 B1
DATED : April 22, 2003
INVENTOR(S) : Unger et al.

It is certified that error appears in the above-identified patent and that said Letters Patent is hereby corrected as shown below:

Column 34,
Line 39, please delete "dipalmatoylphospharidic" and insert
-- dipalmitoylphosphatidic -- therefor.

Signed and Sealed this

Twenty-second Day of March, 2005

JON W. DUDAS
*Director of the United States Patent and Trademark Office*